United States Patent
Iwase et al.

(10) Patent No.: US 12,304,913 B2
(45) Date of Patent: May 20, 2025

(54) DIHYDROPYRROLOPYRAZOLE DERIVATIVE

(71) Applicant: UBE INDUSTRIES, LTD., Ube (JP)

(72) Inventors: Noriaki Iwase, Ube (JP); Yasuhiro Aga, Ube (JP); Shigeyuki Kono, Ube (JP); Tomio Kimura, Ube (JP)

(73) Assignee: UBE INDUSTRIES, LTD., Ube (JP)

( * ) Notice: Subject to any disclaimer, the term of this patent is extended or adjusted under 35 U.S.C. 154(b) by 927 days.

(21) Appl. No.: 17/293,873

(22) PCT Filed: Nov. 13, 2019

(86) PCT No.: PCT/JP2019/044558
§ 371 (c)(1),
(2) Date: May 13, 2021

(87) PCT Pub. No.: WO2020/100944
PCT Pub. Date: May 22, 2020

(65) Prior Publication Data
US 2022/0002303 A1 Jan. 6, 2022

(30) Foreign Application Priority Data
Nov. 14, 2018 (JP) ................ 2018-213807

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................. C07D 487/04
See application file for complete search history.

(56) References Cited

FOREIGN PATENT DOCUMENTS

| EP | 3 309 163 A1 | 4/2018 |
| JP | 2010/505905 A | 2/2010 |
| JP | 2018/502098 A | 1/2018 |
| WO | WO-2008/043745 A1 | 4/2008 |
| WO | WO-2016/105528 A2 | 6/2016 |
| WO | WO-2016/105528 A3 | 6/2016 |
| WO | WO-2016/204153 A1 | 12/2016 |

OTHER PUBLICATIONS

Wislicenus, J. "Adolph Strecker's Short Textbook of Organic Chemistry" 1881, Spottiswoode: London, pp. 38-39.*
Tacke "Drug Design Based on the Carbon/Silicon Switch Strategy" Topics in Medicinal Chemistry (2016), 17, 29-59.*
Sava "CDK7 inhibitors as anticancer drugs" Cancer and Metastasis Reviews (2020) 39:805-823.*
Ettl, T "The Renaissance of Cyclin Dependent Kinase Inhibitors." Cancers 2022, 14, 293.*
Lukasik "Cyclin-Dependent Kinases (CDK) and Their Role in Diseases Development—Review" Int. J. Mol. Sci. 2021, 22, 2935.*
Xia "Selective inhibition of CDK7 ameliorates experimental arthritis in mice" Clin Exp Med (2015) 15:269-275.*
Bendele, "Animal Models of Arthritis: Relevance to Human Disease" Toxicol Pathol 1999 27: 134-142.*
Georg Pilz, "Modern multiple sclerosis treatment—what is approved, what is on the horizon" Drug Discovery Today Dec. 2008, vol. 13, Nos. 23/24 1013-1025.*
Chaichian "Targeted Therapies in Systemic Lupus Erythematosus: A State-of-the-Art Review" J Clin Cell Immunol 2013, S6, 1-8.*
Mahieu "A critical review of clinical trials in systemic lupus erythematosus" Lupus (2016) 25, 1122-1140.*
Kittaka Atsushi, Drug Discovery Science/Medicinal Chemistry, 2007, p. 142-50.
Wermuth, C.G. (editor), "Latest Medicinal Chemistry vol. 1", Technomics, Inc., Aug. 15, 1998, pp. 235-271, Chapter 13, Molecule transformation based on equivalent substitution.
Extended European Search Report mailed on Oct. 18, 2022 for EP Patent Application No. 19883969.8, 7 pages.
International Search Report mailed on Jan. 28, 2020, for PCT/JP2019/044558, filed Nov. 13, 2019, 3 pages.
Jing, L. et al. (May 1, 2018, e-published Mar. 8, 2018). "Discovery of novel CDK inhibitors via scaffold hopping from CAN508," *Bioorg Med Chem Lett* 28(8):1386-1391.
Written Opinion mailed on Jan. 28, 2020, for PCT/JP2019/044558, filed Nov. 13, 2019, 5 pages.

* cited by examiner

*Primary Examiner* — David K O'Dell
(74) *Attorney, Agent, or Firm* — Mintz, Levin, Cohn, Ferris, Glovsky, and Popeo, P.C.

(57) ABSTRACT

The present invention provides a compound represented by general formula (I) or a pharmacologically acceptable salt thereof. [In the formula, the two Rs each independently represents a $C_{1-3}$ alkyl group, or are bonded together to form a $C_{2-5}$ alkylene group, A represents a $C_{6-10}$ aryl group (which may be a substituted $C_{6-10}$ aryl group), Z represents a hydrogen atom or a $C_{1-6}$ alkyl group (which may be a substituted $C_{1-10}$ aryl group), or A and Z may be bonded to each other, with the group represented by Z—N-A forming a bicyclic fused heteroaryl group, which may be substituted, and $R^1$, $R^2$, and $R^3$ each independently represents a linear or branched $C_{1-4}$ alkyl group that may be substituted.]

[Formula 1]

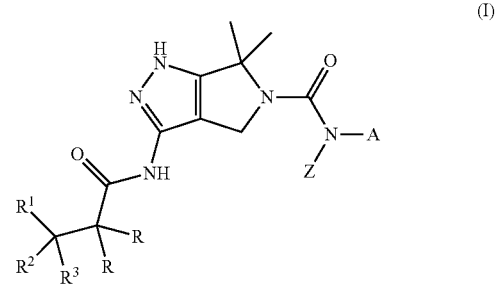

(I)

17 Claims, No Drawings

DIHYDROPYRROLOPYRAZOLE DERIVATIVE

CROSS-REFERENCE TO RELATED APPLICATIONS

This application is a Section 371 US National Phase of International Application No. PCT/JP2019/044558 filed Nov. 13, 2019, which claims priority to Japanese Application No. 2018-213807 filed Nov. 14, 2018.

FIELD OF TECHNOLOGY

The present invention relates to a dihydropyrrolopyrazole derivative, or a pharmacologically acceptable salt thereof, having excellent CDK7 inhibitory activity and useful as a pharmaceutical (for example, a pharmaceutical for treating or preventing cancer, inflammatory diseases, allergic diseases, or chronic respiratory diseases).

PRIOR ART

CDK (cyclin-dependent kinase) is a factor that regulates cell proliferation, involved in entry into DNA synthesis (S phase), cell division (M phase), and the like, of the cell cycle. Many types of CDK are known. Also, CDK is controlled in multiple stages by phosphorylation or dephosphorylation of the threonine residue of the active loop (T-loop) in its three-dimensional structure. When a specific threonine residue of CDK is phosphorylated, a complex with a particular cyclin is formed and activated. The complexes important for cell cycle regulation include CDK1, CDK2/cyclin A, and CDK1/cyclins B1-B3, along with CDK2, CDK4, CDK5, CDK6/cyclins D1-D3, CDK2/cyclin E, each of which is involved in a specific phase of the cell cycle. In a metazoan, CDK7 forms a CDK-activating kinase (CAK: CDK-activating kinase) along with cyclin H and MAT1, and is involved with the phosphorylation of CDK (for example, CDK1, CDK2, CDK4, and CDK6) that is necessary for the progression of the cell cycle (referencing non-patent document 1).

The hyperproliferation of cells due to abnormal activation of CDK cells is a characteristic common to many cancers, and is known to be associated with loss of checkpoint functions involved in cell cycle regulation of cancer cells (referencing non-patent document 2). CDKs are also known to have functions other than cell cycle regulation, where CDK7 is known to phosphorylate serine in the COOH-terminal domain of RNA polymerase II (RNAPII) to promote binding of RNAPII to DNA and elongation, to positively control transcription (referencing non-patent document 3).

CDK7 inhibiting agents have exhibited effectiveness in cell proliferation testing for various types of cancer cells and in mouse-borne cancer models, so are expected to be useful as anti-cancer agents (referencing non-patent documents 4 and 5).

It has been reported in collagen-induced rheumatism model mice that inhibiting CDK7 improves clinical scores and tissue disorders, reduces anti-CII-IgG2α levels and proinflammatory cytokines of interleukin (IL)-6, IL-1β, IL-17, and the like, and reduces levels of Th17 cells (referencing non-patent document 6).

In addition, the CDK7 inhibiting agents that play an important role in cell cycle progression are also expected to be effective in inhibiting viral infections such as HIV, EBV, HCV, and in suppressing cardiac hypertrophy (referencing non-patent documents 7 and 8). In addition to the above, diseases in which CDK7 inhibiting agents are believed to be useful include autoimmune diseases such as psoriasis and multiple sclerosis, neurodegenerative diseases such as Alzheimer's, allergic diseases such as atopic dermatitis, chronic respiratory diseases such as chronic obstructive pulmonary disease (COPD), fibrosis such as idiopathic pulmonary fibrosis, and so forth (referencing, non-patent documents 9 through 11 and referencing non-patent documents 16-18).

PRIOR ART DOCUMENTS

Patent Documents

Patent Document 1: International Publication Number: 2002/012242
Patent Document 2: International Publication Number: 2004/056827
Patent Document 3: International Publication Number: 2004/080457
Patent Document 4: International Publication Number: 2007/068637
Patent Document 5: International Publication Number: 2007/072153
Patent Document 6: International Publication Number: 2007/099171
Patent Document 7: International Publication Number: 2008/043745
Patent Document 8: International Publication Number: 2008/125945
Patent Document 9: International Publication Number: 2011/044264
Patent Document 10: International Publication Number: 2008/151304
Patent Document 11: International Publication Number: 2013/128028
Patent Document 12: International Publication Number: 2013/128029
Patent Document 13: International Publication Number: 2014/063068
Patent Document 14: International Publication Number: 2015/058126
Patent Document 15: International Publication Number: 2015/058140
Patent Document 16: International Publication Number: 2015/058163
Patent Document 17: International Publication Number: 2015/124941
Patent Document 18: International Publication Number: 2015/154022
Patent Document 19: International Publication Number: 2015/154038
Patent Document 20: International Publication Number: 2015/154039
Patent Document 21: International Publication Number: 2016/068287
Patent Document 22: International Publication Number: 2016/204153
Patent Document 23: International Publication Number: 2017/188357
Patent Document 24: International Publication Number: 2017/188358
Patent Document 25: International Publication Number: 2017/188369

Non-Patent Documents

Non-Patent Document 1: Journal of Cell Science 2005, 118 (20), 5171-5180.

Non-Patent Document 2: Nature Reviews Cancer 2009, 9, 153-166.
Non-Patent Document 3: Biochim Biophys Acta 2004, 1677, 64-73.
Non-Patent Document 4: Nature 2014, 511, 616-620.
Non-Patent Document 5: Cancer Res 2009, 69, 6208-6215.
Non-Patent Document 6: Clin Exp Med 2015, 15, 269-275.
Non-Patent Document 7: Curr HIV Res 2003, 1 (2), 131-152.
Non-Patent Document 8: Mol Cell Biol 1998, 18 (11), 6729-6736).
Non-Patent Document 9: Br J Dermatol 2000, 143 (5), 950-956.
Non-Patent Document 10: Biochem Biophys Res Commun 2013, 435 (3), 378-384.
Non-Patent Document 11: Neurobiol Aging 2000, 6, 807-813.
Non-Patent Document 12: J Med Chem 2012, 55 (10), 4728-4739.
Non-Patent Document 13: Bioorganic & Medicinal Chemistry 2010, 18 (5), 1844-1853.
Non-Patent Document 14: Chem Med Chem 2007, 2, 841-852.
Non-Patent Document 15: Current Drug Targets, 2010, 11, 291-302.
Non-Patent Document 16: Clinical & Experimental Allergy, 2011, 41, 673-687.
Non-Patent Document 17: Cell Death and Differentiation, 2012, 19, 1950-1961.
Non-Patent Document 18: Am J Physiol Lung Cell Mol 2004, 286, 727-733.

SUMMARY OF THE INVENTION

Problem Solved by the Present Invention

As compounds that inhibit CDK7, the compounds described in patent documents 10 through 22 and non-patent document 4 are reported to have CDK7 inhibitory activity.
However, not many compounds having excellent CDK7 inhibitory activity are known (referencing non-patent document 15). Given this, an object of the present invention is to provide a new compound having excellent CDK7 inhibitory activity.

Means for Solving the Problem

The present inventors discovered that dihydropyrrolopyrazole compounds having a specific structure, and pharmacologically acceptable salts thereof, have excellent CDK7 inhibitory activity, thereby arriving at the present invention.
Note that patent documents 1 through 9 and 12 through 14 disclose compounds having a 6,6-dimethyl-4,6-dihydropyrrolo [3,4-c]pyrazole skeleton, but there is no disclosure of CDK7 inhibitory activity.
The present invention provides: a dihydropyrrolopyrazole compound, and a pharmacologically acceptable salt thereof, having excellent CDK7 inhibitory activity; a pharmaceutical composition including a dihydropyrrolopyrazole compound or pharmacologically acceptable salt thereof as active ingredient, that is well suited for the treatment or prevention of cancer, benign tumors, angiogenesis, inflammatory diseases (for example, autoimmune diseases), viral infections (HIV, EBV, HCV, etc.), neurodegenerative diseases (for example, Alzheimer's disease), allergic diseases (for example, atopic dermatitis), chronic respiratory diseases (for example, chronic obstructive disease (COPD)), fibrosis (for example, idiopathic pulmonary fibrosis), cardiovascular diseases such as cardiac hypertrophy, and erectile dysfunction;
the use of a dihydropyrrolopyrazole compound, or a pharmacologically acceptable salt thereof, for the treatment or prevention (preferably, treatment) of disorders (preferably the disorders listed above);
a method for the treatment or prevention (preferably, treatment) of disorders (preferably, the disorders listed above) by administering a therapeutically effective amount of a dihydropyrrolopyrazole compound, or a pharmacologically acceptable salt thereof, to a warm-blooded animal (preferably, a human); and
a method for manufacturing the dihydropyrrolopyrazole compound or pharmacologically acceptable salt thereof, or intermediate thereof.
The cancer may be a cancer that is treatable by inhibition of CDK7, for example, bladder cancer, breast cancer, colon cancer (for example, colorectal cancer, such as colon adenocarcinoma or colon adenoma), kidney cancer, epidermal cancer, liver cancer, lung cancer (for example, adenocarcinoma, small cell lung cancer, non-small cell lung cancer), esophageal cancer, gallbladder cancer, ovarian cancer, pancreatic cancer (for example, pancreatic endocrine tumor), gastric cancer, cervical cancer, endometrial cancer, thyroid cancer, nasal cancer, head and neck cancer, prostate cancer, cutaneous cancer (for example, melanoma, squamous cell carcinoma), lymphoid hematopoietic tumors (for example, leukemia, acute lymphocytic leukemia, chronic lymphocytic leukemia, B-cell lymphoma (for example, leukemia, acute lymphocytic leukemia, chronic lymphocytic leukemia, B-cell lymphoma), diffuse large cell B-cell lymphoma), T-cell lymphoma, multiple myeloma, Hodgkin's lymphoma, non-Hodgkin's lymphoma, pilocytic lymphoma, Burkitt's lymphoma), bone marrow-based hematopoietic tumors (for example, acute or chronic myeloid leukemia, myelodysplastic syndrome, pre-myelocytic leukemia), tumors of mesenchymal origin (for example, fibrosis sarcoma, Ewing's sarcoma, striated muscle sarcoma), tumors of the central or peripheral nervous system (for example, astrocytoma, neuroblastoma, glioma, brain tumors, Schwannoma), epithelioma, taratoma, osteosarcoma, xeroderma pigmentosum, keratoacanthoma, thyroid follicular cancer, and Kaposi's sarcoma. The cancer is preferably bladder cancer, breast cancer, colon cancer, kidney cancer, liver cancer, lung cancer, esophageal cancer, gallbladder cancer, ovarian cancer, pancreatic cancer, stomach cancer, cervical cancer, thyroid cancer, head and neck cancer, prostate cancer, cutaneous cancer, a tumor of mesenchymal origin, a tumor of the central or peripheral nervous system, a hematopoietic tumor of the lymphatic system, a hematopoietic tumor of the myeloid system, a teratoma, an osteosarcoma, or a Kaposi's sarcoma. The autoimmune disease should be an autoimmune disease that can be treated by inhibition of CDK7, which may be, for example, multiple sclerosis, Guillain-Barre syndrome, myasthenia gravis, chronic atrophic gastritis, autoimmune hepatitis, primary biliary cirrhosis, primary sclerosing cholangitis, autoimmune pancreatitis, aortic arch syndrome, Goodpasture's syndrome, rapidly progressive glomerulonephritis, megakaryoblastic anemia, autoimmune hemolytic anemia, autoimmune neutrophil depletion, idiopathic thrombocytopenic purpura, Basedow's disease, Hashimoto's disease, primary thyroid dysfunction, idiopathic Addison disease, type 1 diabetes, circumscribed scleroderm, acquired epidermolysis bullosa, vitiligo vulgaris, autoimmune optic neuropathy, autoimmune inner ear disorder, idiopathic azoospermia, rheumatoid arthritis, systemic lupus erythematosus, drug-induced lupus, Sjogren's syndrome, polymyositis, psoriasis, dermatomyositis, scleroderma, vasculitis syndrome, mixed connective tissue disease, or inflammatory bowel disease (e.g., Crohn's disease, ulcerative colitis). Here, "inflammatory bowel disease" (IBD) is a general term for any disease that causes chronic inflammation or ulceration of the mucosa of the colon or small intestine.

The present invention provides the following [Aspect 1] through [Aspect 54] as one aspect thereof.

[Aspect 1] A compound represented by general formula (I) or a pharmacologically acceptable salt thereof:

[Formula 1]

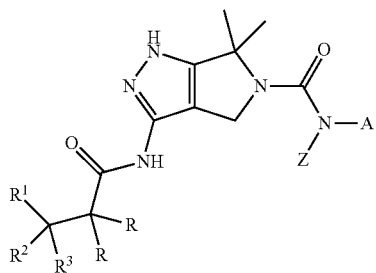

(I)

[In the formula, the two Rs each independently represents a $C_{1-3}$ alkyl group, or are bonded together to form a $C_{2-5}$ alkylene group, A represents a $C_{6-10}$ aryl group (which may be a substituted $C_{6-10}$ aryl group) or a heteroaryl group (which may be a substituted heteroaryl group), Z represents a hydrogen atom or a $C_{1-6}$ alkyl group (which may be a substituted $C_{1-6}$ alkyl), or A and Z may be bonded to each other, with the group represented by Z—N-A forming a bicyclic fused heteroaryl group, which may be substituted, and $R^1$, $R^2$, and $R^3$ each independently represents a linear or branched $C_{1-4}$ alkyl group that may be substituted.]

[Aspect 2] A compound represented by general formula (II) or a pharmacologically acceptable salt thereof:

[Formula 2]

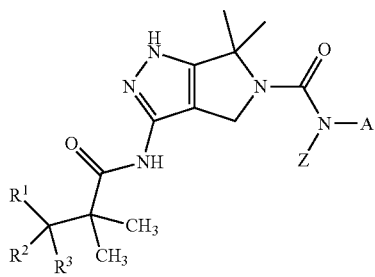

(II)

[In the formula, A represents a $C_{6-10}$ aryl group (which may be a substituted $C_{6-10}$ aryl group) or a heteroaryl group (which may be a substituted heteroaryl group), Z represents a hydrogen atom or a $C_{1-6}$ alkyl group (which may be a substituted $C_{1-6}$ alkyl group), or A and Z may be bonded to each other, with the group represented by Z—N-A forming a bicyclic fused heteroaryl group, which may be substituted, and $R^1$, $R^2$, and $R^3$ each independently represents a linear or branched $C_{1-4}$ alkyl group that may be substituted.]

[Aspect 3] A compound represented by general formula (III) or a pharmacologically acceptable salt thereof:

[Formula 3]

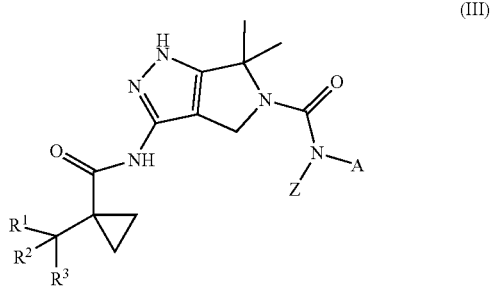

(III)

[In the formula, A represents a $C_{6-10}$ aryl group (which may be a substituted $C_{6-10}$ aryl group) or a heteroaryl group (which may be a substituted heteroaryl group), Z represents a hydrogen atom or a $C_{1-6}$ alkyl group (which may be a substituted $C_{1-6}$ alkyl), or A and Z may be bonded to each other, with the group represented by Z—N-A forming a bicyclic fused heteroaryl group, which may be substituted, and $R^1$, $R^2$, and $R^3$ each independently represents a linear or branched $C_{1-4}$ alkyl group that may be substituted.]

[Aspect 4] A compound represented by general formula (IV) or a pharmacologically acceptable salt thereof:

[Formula 4]

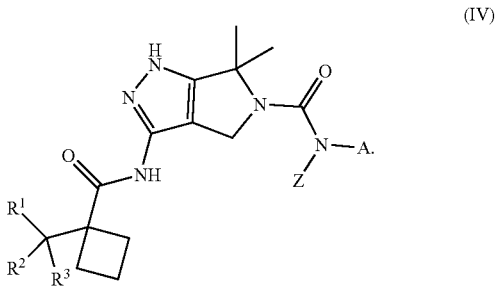

(IV)

[In the formula, A represents a $C_{6-10}$ aryl group (which may be a substituted $C_{6-10}$ aryl group) or a heteroaryl group (which may be a substituted heteroaryl group), Z represents a hydrogen atom or a $C_{1-6}$ alkyl group (which may be a substituted $C_{1-6}$ alkyl), or A and Z may be bonded to each other, with the group represented by Z—N-A forming a bicyclic fused heteroaryl group, which may be substituted, and $R^1$, $R^2$, and $R^3$ each independently represents a linear or branched $C_{1-4}$ alkyl group that may be substituted.]

[Aspect 5] A compound selected from the following, or a pharmacologically acceptable salt thereof:
3-(1-(tert-butyl) cyclobutane-1-carboxamide)-N-(2-fluorophenyl)-6,6-dimethyl-4,6-dihydropyrrolo [3,4-c]pyrazole-5 (1H)-carboxamide,
3-(1-(tert-butyl) cyclobutane-1-carboxamide)-N-(o-tolyl)-6,6-dimethyl-4,6-dihydropyrrolo [3,4-c]pyrazole-5 (1H)-carboxamide, 3-(1-(tert-butyl) cyclobutane-1-carboxamide)-N-(2-chloro-6-methylphenyl)-6,6-dimethyl-4,6-dihydropyrrolo [3,4-c] pyrazole-5 (1H)-carboxamide,
3-(1-(tert-butyl) cyclobutane-1-carboxamide)-N-(5-fluoro-2-methylphenyl)-6,6-dimethyl-4,6-dihydropyrrolo [3,4-c] pyrazole-5 (1H)-carboxamide,
3-(1-(tert-butyl) cyclobutane-1-carboxamide)-N-(2,5-dimethylphenyl)-6,6-dimethyl-4,6-dihydropyrrolo [3,4-c] pyrazole-5 (1H)-carboxamide,
3-(1-(tert-butyl) cyclobutane-1-carboxamide)-N-(2,6-dimethylchlorophenyl)-6,6-dimethyl-4,6-dihydropyrrolo [3,4-c]pyrazole-5 (1H)-carboxamide,
3-(1-(tert-butyl) cyclobutane-1-carboxamide)-N-(2-chloro-6-fluorophenyl)-6,6-dimethyl-4,6-dihydropyrrolo [3,4-c] pyrazole-5 (1H)-carboxamide,
N-(2-bromo-6-methylphenyl)-3-(1-(tert-butyl) cyclobutane-1-carboxamide)-6,6-dimethyl-4,6-dihydropyrrolo [3,4-c] pyrazole-5 (1H)-carboxamide,
3-(1-(tert-butyl) cyclobutane-1-carboxamide)-N-(2-fluoro-3,6-dimethylphenyl)-6,6-dimethyl-4,6-dihydropyrrolo [3,4-c]pyrazole-5 (1H)-carboxamide,
3-(1-(tert-butyl) cyclobutane-1-carboxamide)-N-(6-fluorobenzofuran-7-yl)-6,6-dimethyl-4,6-dihydropyrrolo [3,4-c]pyrazole-5 (1H)-carboxamide, and
3-(1-(tert-butyl) cyclobutane-1-carboxamide)-N-(2-chloro-6-fluorobenzofuran-7-yl)-6,6-dimethyl-4,6-dihydropyrrolo [3,4-c]pyrazole-5 (1H)-carboxamide.

[Aspect 6]A pharmaceutical composition containing a compound or pharmacologically acceptable salt thereof set forth in any of [Aspect 1] through [Aspect 5].

[Aspect 7]A pharmaceutical composition set forth in [Aspect 6], being a CDK7 inhibiting agent.

[Aspect 8]A pharmaceutical composition set forth in [Aspect 6] or [Aspect 7], for the treatment or prevention of a cancer, an inflammatory disease, an allergic disease, or a chronic respiratory disease.

[Aspect 9]A pharmaceutical composition set forth in Aspect 8, wherein the above cancer is a hematological cancer or a solid cancer.

[Aspect 10]A pharmaceutical composition set forth in [Aspect 9], wherein the hematological cancer is multiple myeloma, chronic myelogenous leukemia, a hematological tumor, a hematologic malignancy, childhood leukemia, a childhood lymphoma, Hodgkin's disease, a lymphocytic lymphoma, a cutaneous lymphoma, acute leukemia, chronic leukemia, acute lymphoblastic leukemia, acute myelocytic leukemia, chronic myelocytic leukemia, a plasma cell neoplasm, a lymphocyte-like neoplasm, or an AIDS-related cancer.

[Aspect 11]A pharmaceutical composition set forth in [Aspect 9], wherein the solid cancer is bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer (including squamous cell carcinoma), a fibrosarcoma, a rhabdomyosarcoma, an astrocytoma, a neuroblastoma, a glioma or schwannoma, a melanoma, a seminoma, a teratoid carcinoma, an osteosarcoma, a xeroderma pigmentosum, a keratinocytoma, a follicular carcinoma of the thyroid, or a Kaposi's sarcoma.

[Aspect 12]A pharmaceutical composition set forth in any of [Aspect 8] through [Aspect 11], wherein the inflammatory disease is an autoimmune disease.

[Aspect 13]A pharmaceutical composition set forth in [Aspect 12], wherein the autoimmune disease is rheumatoid arthritis, psoriasis, multiple sclerosis, or inflammatory bowel disease.

[Aspect 14]A pharmaceutical composition set forth in any of [Aspect 8] through [Aspect 13], wherein the allergic disease is atopic dermatitis.

[Aspect 15]A pharmaceutical composition set forth in any of [Aspect 8] through [Aspect 14], wherein the chronic respiratory disease is chronic obstructive pulmonary disease.

[Aspect 16]A pharmaceutical composition set forth in any of [Aspect 6] through [Aspect 15], administered in combination with one or more other drugs selected from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs.

[Aspect 17]A pharmaceutical composition set forth in any of [Aspect 6] through [Aspect 15], administered simultaneously with, or at different times from, a composition that has, as an active ingredient, one or more other drugs selected from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs.

[Aspect 18]A pharmaceutical composition set forth in any of [Aspect 6] through [Aspect 15], further including, as an active ingredient, one or more other drugs selected from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs.

[Aspect 19]A pharmaceutical composition set forth in any of [Aspect 16] through [Aspect 18], wherein an other drug is a selection from a group comprising tyrosine kinase inhibiting agents, immune checkpoint inhibiting agents, DNA alkylating agents, DNA synthesis inhibiting agents, platinum preparations, metabolic antagonists, topoisomerase I inhibiting agents, topoisomerase II inhibiting agents, tubulin agonists, hormone antagonists, aromatase inhibiting agents, differentiation inducers, proteosome inhibiting agents, phospholipid kinase inhibiting agents, adenosine deaminase inhibiting agents, angiogenesis inhibiting agents, histone deacetylase (HDAC) inhibiting agents, BET bromodomain inhibiting agents, histone demethylase inhibiting agents, histone methyltransferase inhibiting agents, matrix metalloproteinase inhibiting agents, farnesyl transferase inhibiting agents, bisphosphonates, Hsp90 inhibiting agents, kinesin Eg5 inhibiting agents, serine threonine kinase inhibiting agents, anticytokine agents, immunosuppressive agents, immunomodulators, topically active vitamin D3, SiP1 receptor antagonists, interferon preparations, anticholinergic agents, leukotoluene antagonists, PDE4 inhibiting agents, prostaglandin (PG) D2 receptor antagonists, neutrophil elastase inhibiting agents, antihistamines, classic nonsteroidal anti-inflammatory drugs, cyclooxygenase inhibiting agents, nitric oxide-free nonsteroidal anti-inflammatory agents, gold preparations, penicillamine, aminosalicylic acid preparations, antimalarial agents, pyrimidine synthesis inhibiting agents, TNF inhibiting agents, interleukin inhibiting agents, interleukin receptor antagonists, interleukin receptor agonists, B-cell activation inhibiting agents, co-stimulating molecule-related protein preparations, MAPK inhibiting agents, gene modulators, cytokine production inhibiting agents, TNF α converting enzyme inhibiting agents, IL-1β converting enzyme inhibiting agents, chemokine antagonists, therapeutic vaccines, gene therapy drugs, antisense compounds, proteasome inhibiting agents, JAK inhibiting agents, T-cell inhibiting agents, inosine monophosphate dehydrogenase (IMPDH) inhibiting agents, adhesion molecule inhibiting agents, thalidomide, cathepsin inhibiting agents, glucose-6-phosphate dehydrogenase inhibiting agents, dihydroorotate dehydrogenase (DHODH) inhibiting agents, phospholipase A2 inhibiting agents, iNOS inhibiting agents, microtubule stimulating agents, microtubule inhibiting agents, MHC class II antagonists, CD4 antagonists, CD23 antagonists, leukotriene B4 receptor antagonists, 5-lipoxygenase inhibiting agents, cathepsin B inhibiting agents, osteogenesis stimulating agents, dipeptidyl peptidase inhibiting agents, collagen agonists, capsaicin creams, sulfa drugs, hyaluronic acid derivatives, glucosamine sulfate, amiprilose, CD20 inhibiting agents, CD52 inhibiting agents, anti-asthma drugs, atopic dermatitis medications, allergic rhinitis medications, opioid receptor agonists, immunoglobulins, glatiramer acetate, T-cell receptor vaccines, adhesion molecule inhibiting agents, muscle relaxants, local anesthetics, ketamine, short- and long-acting muscarin receptor antagonists, short- and long-acting beta-receptor agonists, inhaled steroids, oral steroids, mixtures of p receptor agonists and inhaled steroids, vitamin derivatives, and adrenal corticosteroids.

[Aspect 20]A pharmaceutical composition set forth in any of [Aspect 16] through [Aspect 18], wherein an other drug is a selection from a group comprising Doxorubicin, Taxotere, Taxol, Etoposide, Irinotecan, Topotecan, Paclitaxel, Docetaxel, Epothilone, Tamoxifen, Fluorouracil, Fingolimod, Methotrexate, Temozolomide, Cyclophosphamide, SCH 66336, R115777, L778,123, BMS 214662, Gefitinib, Erlotinib, Panitumumab, Afatinib, Dasatinib, Bosutinib, Vandetanib, Sunitinib, Axitinib, Pazopanib, Lenvatinib, Lapatinib, Nintedanib, Nilotinib, Crizotinib, Ceritinib, Alectinib, Ibrutinib, Imatinib, Sorafenib, Vemurafenib, Dabrafenib, Trametinib, Palbociclib, Interferon alfa-2b, Cytarabine, Adriamycin, Cytoxan, Gemcitabine, Uramustine, Chlormethine, Ifosfamide, Melphalan, Chlorambucil, Pipobroman, Triethylenemelamine, Triethylenethiophosphoramin, Ofatumumab, Busulfan, Carmustine, Lomustine, Streptozotocin, Dacarbazine, Floxuridine, 6-Mercaptopurine, 6-Tioguanine, Regorafenib, Ramucirumab, Fludarabine Phosphate, Oxaliplatin, Folinate, Pentostatin, Vinblastine, Vincristine, Vindesine, Bleomycin, Dactinomycin, Daunorubicin, Doxorubicin, Epirubicin, Idarubicin, Mithramycin, Deoxycoformycin, Mitomycin C, L-asparaginase, Teniposide, 17α-Ethynylestradiol, diethylstilbestrol, testosterone, prednisone, Fluoxymesterone, dromostanolone propionate, Testolactone, Megestrol acetate, Methylprednisolone, Methyltestosterone, Prednisolone, Chlorotrianisene, 17-Hydroxyprogesterone, Aminoglutethimide, Estramustine, Medroxyprogesterone acetate, Leuprolide Acetate, Flutamide, Toremifene, Goserelin, Carboplatin, Hydroxycarbamide, Amsacrine, Procarbazine, Mitotane, Mitoxantrone, Levamisole, Navelbine, Anastrozole, Letrazole, Capecitabine, Reloxafine, Droloxifene, hexamethylmelamine, Bevacizumab, Omalizumab, Mepolizumab, Gemtuzumab ozogamicin, Mogamulizumab, Pertuzumab, Ocrelizumab, Alemtuzumab, Inotuzumab, Tositumomab, Bortezomib, Ibritumomab tiuxetan, arsenic trioxide, Vinorelbine, Porfimer, Thiotepa, Altretamine, Trastuzumab, Letrozole, Fulvestrant, Exemestane, Rituximab, Cetuximab, Basiliximab, Nivolumab, Ipilimumab, Pembrolizumab, Durvalumab, Atezolizumab, Avelumab, Alcofenac, Aceclofenac, Sulindac, Tolmetin, Etodolac, Fenoprofen, Tiaprofenic acid, Meclofenamic acid, Meloxicam, Tenoxicam, Lornoxicam, Nabumetone, Acetaminophen, Phenacetin, Ethenzamide, Sulpyrine, Antipyrine, Migrenin, aspirin, mefenamic acid, flufenamic acid, Phenylbutazone, Indomethacin, ibuprofen, ketoprofen, naproxen, oxaprozin, Flurbiprofen, Fenbufen, Pranoprofen, floctafenine, Piroxicam, Epirizole, Tiaramide hydrochloride, Zaltoprofen, Gabexate Mesilate, Camostat Mesilate, Ulinastatin, Colchicine, Probenecid, Sulfinpyrazone, Benzbromarone, Allopurinol, Brentuximab vedotin, sodium aurothiomalate, sodium hyaluronate, Atropine, Scopolamine, Morphine or a salt thereof, Pethidine, Levorphanol, Oxymorphone, Celecoxib, Etoricoxib, Valdecoxib, Loxoprofen, Auranofin, D-Penicillamine, Sulfasalazine, Mesalamine, Olsalazine, Balsalazide, Chloroquine, Leflunomide, Tacrolimus, Infliximab, Etanercept, Adalimumab, Certolizumab pegol, Golimumab, PASSTNFα, soluble TNFα receptor, TNFα binding protein, anti-TNFα antibody, Denosumab, Anakinra, soluble IL-1 receptor antibody, Tocilizumab, anti-IL-6 antibody, IL-10, Ustekinumab, Briakinumab, Secukinumab (aka AIN-457), Ixekizumab (aka LY-2439821), AMG827, Rituximab, Belimumab, Abatacept, BMS-582949, inhibiting agents for molecules involved in signal transduction, MAPK inhibiting agents, salicylic acid ointments, urea ointments, Iguratimod, Tetomilast, Belnacasan, HMPL-004, IL-8 antagonists, CXCR1-CXCR2 dual antagonists, Reparixin, CCR9 antagonists, Denileukin Diftitox, CCX025, N-{4-chloro-2-[(1-oxydopyridin-4-yl) carbonyl]phenyl}-4-(propan-2-yloxy) benzenesulfonamide, MCP-1 antagonists, Irbesartan, TNFα vaccines, ISIS-104838, Natalizumab, Vedolizumab, AJM300, TRK-170, E6007, MX-68, BMS-188667, CKD-461, Rimexolone, Cyclosporin A, Mizoribine, Gusperimus, Sirolimus, Temsirolimus, Everolimus, antlymph serums, dried sulfated immunoglobulin, erythropoietin, colony-stimulating factor, atiprimod dihydrochloride, Azathioprine, interferon α, interferon β1b, interferon β1a, Tofacitinib, Baricitinib, Carfilzomib, Ruxolitinib, Dexamethasone, Hexestrol, Thiamazole, Betamethasone, Triamcinolone Acetonide, Fluocinonide, Fluocinolone acetonide, cortisone acetate, hydrocortisone, Fluorometholone, Beclometasone, Estriol, Mycophenolate mofetil, sodium alicaforsen, selectin inhibiting agents, ELAM-1 inhibiting agents, VCAM-1 inhibiting agents, ICAM-1 inhibiting agents, V-85546, Roflumilast, Apremilast, VAS203, Reumacon, Zanolimumab, DW-1350, Zileuton, Tyk2 inhibiting agents, Synvisc (hylan G-F 20), Orthovisc, Atacicept, Blisibimod, Tizanidine, Eperisone, Afloqualone, Baclofen, diazepam, Dantrolene, vitamin D3 derivatives, vitamin D2 derivatives, Isoprenaline hydrochloride, Salbutamol sulfate, Procaterol hydrochloride, Terbutaline sulfate, Trimetoquinol hydrochloride, Tulobuterol hydrochloride, Orciprenaline sulfate, Fenoterol hydrobromide, ephedrine hydrochloride, ipratropium bromide, oxytropium bromide, Flutropium bromide, Theophylline, Aminophylline, sodium cromoglicate, Tranilast, Repirinast, Anlexanone, Ibudilast, Ketotifen, Terfenadine, Mequitazine, Azelastine, Ozagrel hydrochloride, Pranlukast hydrate, seratrodast, Ciclesonide, Chlorpheniramine maleate, Alimemazine tartrate, Clemastine fumarate, Homochlorcyclizine hydrochloride, Fexofenadine, Ketotifen fumarate, Cetirizine hydrochloride, Oxatomide, Ebastine, Epinastine hydrochloride, Loratadine, Tramadol, Promethazine, Hydroxyzine, Homochlorcyclizine, Cyproheptadine, Mequitazine, Emedastine, pseudoephedrine, Bepotastine besilate, Levocetirizine, Olopatadine hydrochloride, Mycophenolate mofetil, Daclizumab, Galiximab, Metformin hydrochloride, Visilizumab, Aminopterin, Pazopanib hydrochloride, Fezakinumab, Ruxolitinib phosphate, Ixekizumab, Guselkumab, SLx-2119, PRX-167700, Lidocaine, Tiotropium bromide, Salmeterol xinafoate, Formoterol fumarate, Fluticasone propionate, Beclometasone, Budesonide, and combination drugs of Salmeterol xinafoate and Fluticasone propionate.

[Aspect 21] A pharmaceutical composition set forth in any of [Aspect 16] through [Aspect 18], wherein an other drug is 5-fluorouracil, oxaliplatin, or irinotecan.

[Aspect 22] A method for treating or preventing cancer, an inflammatory disease, an allergic disease, or a chronic respiratory disease, including administration of a compound set forth in any of [Aspect 1] through [Aspect 6], or a pharmacologically acceptable salt thereof, to a subject in need thereof.

[Aspect 23] A method set forth in [Aspect 22], wherein the above cancer is a hematological cancer or a solid cancer.

[Aspect 24] A method set forth in [Aspect 23], wherein the hematological cancer is a selection from a group comprising multiple myeloma, chronic myelogenous leukemia, a hematological tumor, a hematologic malignancy, childhood leukemia, a childhood lymphoma, Hodgkin's disease, a lymphocytic lymphoma, a cutaneous lymphoma, acute leukemia, chronic leukemia, acute lymphoblastic leukemia, acute myelocytic leukemia, chronic myelocytic leukemia, a plasma cell neoplasm, a lymphocyte-like neoplasm, or an AIDS-related cancer.

[Aspect 25] A method set forth in [Aspect 23], wherein the solid cancer is a selection from a group comprising bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer (including squamous cell carcinoma), a fibrosarcoma, a rhabdomyosarcoma, an astrocytoma, a neuroblastoma, a glioma or schwannoma, a melanoma, a seminoma, a teratoid carcinoma, an osteosarcoma, a xeroderma pigmentosum, a keratinocytoma, a follicular carcinoma of the thyroid, or a Kaposi's sarcoma.

[Aspect 26] A method set forth in [Aspect 22], wherein the inflammatory disease is an autoimmune disease.

[Aspect 27] A method set forth in [Aspect 26], wherein the autoimmune disease is rheumatoid arthritis, psoriasis, multiple sclerosis, or inflammatory bowel disease.

[Aspect 28] A method set forth in [Aspect 22], wherein the allergic disease is atopic dermatitis.

[Aspect 29] A method set forth in [Aspect 22], wherein the chronic respiratory disease is chronic obstructive pulmonary disease.

[Aspect 30] A method set forth in any of [Aspect 22] through [Aspect 29], wherein one or more other drugs selected from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs is administered in combination.

[Aspect 31] A method set forth in any of [Aspect 22] through [Aspect 29], wherein the compound, or a pharmacologically acceptable salt thereof, is administered simultaneously with, or at different times from, a composition that has, as an active ingredient, one or more selections from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs.

[Aspect 32] A method set forth in any of [Aspect 22] through [Aspect 29], wherein the administration of the compound, or a pharmacologically acceptable salt thereof, is through administering a composition that includes the compound, or a pharmacologically acceptable salt thereof, and a composition that has, as an active ingredient, one or more other drugs selected from a group consisting of anticancer drugs, antirheumatic drugs, psoriasis drugs, multiple sclerosis drugs, inflammatory bowel disease drugs, chronic obstructive pulmonary disease drugs, and atopic dermatitis drugs.

[Aspect 33] A method set forth in any of [Aspect 30] through [Aspect 32], wherein an other drug is a selection from a group comprising tyrosine kinase inhibiting agents, immune checkpoint inhibiting agents, DNA alkylating agents, DNA synthesis inhibiting agents, platinum preparations, metabolic antagonists, topoisomerase I inhibiting agents, topoisomerase II inhibiting agents, tubulin agonists, hormone antagonists, aromatase inhibiting agents, differentiation inducers, proteosome inhibiting agents, phospholipid kinase inhibiting agents, adenosine deaminase inhibiting agents, angiogenesis inhibiting agents, histone deacetylase (HDAC) inhibiting agents, BET bromodomain inhibiting agents, histone demethylase inhibiting agents, histone methyltransferase inhibiting agents, matrix metalloproteinase inhibiting agents, farnesyl transferase inhibiting agents, bisphosphonates, Hsp90 inhibiting agents, kinesin Eg5 inhibiting agents, serine threonine kinase inhibiting agents, anticytokine agents, immunosuppressive agents, immunomodulators, topically active vitamin D3, S1P1 receptor antagonists, interferon preparations, anticholinergic agents, leukotoluene antagonists, PDE4 inhibiting agents, prostaglandin (PG) D2 receptor antagonists, neutrophil elastase inhibiting agents, antihistamines, classic non-steroidal anti-inflammatory drugs, cyclooxygenase inhibiting agents, nitric oxide-free nonsteroidal anti-inflammatory agents, gold preparations, penicillamine, aminosalicylic acid preparations, antimalarial agents, pyrimidine synthesis inhibiting agents, TNF inhibiting agents, interleukin inhibiting agents, interleukin receptor antagonists, interleukin receptor agonists, B-cell activation inhibiting agents, co-stimulating molecule-related protein preparations, MAPK inhibiting agents, gene modulators, cytokine production inhibiting agents, TNF α converting enzyme inhibiting agents, IL-10 converting enzyme inhibiting agents, chemokine antagonists, therapeutic vaccines, gene therapy drugs, antisense compounds, proteasome inhibiting agents, JAK inhibiting agents, T-cell inhibiting agents, inosine monophosphate dehydrogenase (IMPDH) inhibiting agents, adhesion molecule inhibiting agents, thalidomide, cathepsin inhibiting agents, glucose-6-phosphate dehydrogenase inhibiting agents, dihydroorotate dehydrogenase (DHODH) inhibiting agents, phospholipase A2 inhibiting agents, iNOS inhibiting agents, microtubule stimulating agents, microtubule inhibiting agents, MHC class II antagonists, CD4 antagonists, CD23 antagonists, leukotriene B4 receptor antagonists, 5-lipoxygenase inhibiting agents, cathepsin B inhibiting agents, osteogenesis stimulating agents, dipeptidyl peptidase inhibiting agents, collagen agonists, capsaicin creams, sulfa drugs, hyaluronic acid derivatives, glucosamine sulfate, amiprilose, CD20 inhibiting agents, CD52 inhibiting agents, anti-asthma drugs, atopic dermatitis medications, allergic rhinitis medications, opioid receptor agonists, immunoglobulins, glatiramer acetate, T-cell receptor vaccines, adhesion molecule inhibiting agents, muscle relaxants, local anesthetics, ketamine, short- and long-acting muscarin receptor antagonists, short- and long-acting beta-receptor agonists, inhaled steroids, oral steroids, mixtures of R receptor agonists and inhaled steroids, vitamin derivatives, and adrenal corticosteroids.

[Aspect 34] A method set forth in any of [Aspect 30] through [Aspect 32], wherein an other drug is a selection from a group comprising Doxorubicin, Taxotere, Taxol, Etoposide, Irinotecan, Topotecan, Paclitaxel, Docetaxel, Epothilone, Tamoxifen, Fluorouracil, Fingolimod, Methotrexate, Temozolomide, Cyclophosphamide, SCH 66336, R115777, L778,123, BMS 214662, Gefitinib, Erlotinib, Panitumumab, Afatinib, Dasatinib, Bosutinib, Vandetanib, Sunitinib, Axitinib, Pazopanib, Lenvatinib, Lapatinib, Nintedanib, Nilotinib, Crizotinib, Ceritinib, Alectinib, Ibrutinib, Imatinib, Sorafenib, Vemurafenib, Dabrafenib, Trametinib, Palbociclib, Interferon alfa-2b, Cytarabine, Adriamycin, Cytoxan, Gemcitabine, Uramustine, Chlormethine, Ifosfamide, Melphalan, Chlorambucil, Pipobroman, Triethylenemelamine, Triethylenethiophosphoramin, Ofatumumab, Busulfan, Carmustine, Lomustine, Streptozotocin, Dacarbazine, Floxuridine, 6-Mercaptopurine, 6-Tioguanine, Regorafenib, Ramucirumab, Fludarabine Phosphate, Oxaliplatin, Folinate, Pentostatin, Vinblastine, Vincristine, Vindesine, Bleomycin, Dactinomycin, Daunorubicin, Doxorubicin, Epirubicin, Idarubicin, Mithramycin, Deoxycoformycin, Mitomycin C, L-asparaginase, Teniposide, 17α-Ethynylestradiol, diethylstilbestrol, testosterone, prednisone, Fluoxymesterone, dromostanolone propionate, Testolactone, Megestrol acetate, Methylprednisolone, Methyltestosterone, Prednisolone, Chlorotrianisene, 17-Hydroxyprogesterone, Aminoglutethimide, Estramustine, Medroxyprogesterone acetate, Leuprolide Acetate, Flutamide, Toremifene, Goserelin, Carboplatin, Hydroxycarbamide, Amsacrine, Procarbazine, Mitotane, Mitoxantrone, Levamisole, Navelbine, Anastrozole, Letrazole, Capecitabine, Reloxafine, Droloxifene, hexamethylmelamine, Bevacizumab, Omalizumab, Mepolizumab, Gemtuzumab ozogamicin, Mogamulizumab, Pertuzumab, Ocrelizumab, Alemtuzumab, Inotuzumab, Tositumomab, Bortezomib, Ibritumomab tiuxetan, arsenic trioxide, Vinorelbine, Porfimer, Thiotepa, Altretamine, Trastuzumab, Letrozole, Fulvestrant, Exemestane, Rituximab, Cetuximab, Basiliximab, Nivolumab, Ipilimumab, Pembrolizumab, Durvalumab, Atezolizumab, Avelumab, Alcofenac, Aceclofenac, Sulindac, Tolmetin, Etodolac, Fenoprofen, Tiaprofenic acid, Meclofenamic acid, Meloxicam, Tenoxicam, Lornoxicam, Nabumetone, Acetaminophen, Phenacetin, Ethenzamide, Sulpyrine, Antipyrine, Migrenin, aspirin, mefenamic acid, flufenamic acid, Phenylbutazone, Indomethacin, ibuprofen, ketoprofen, naproxen, oxaprozin, Flurbiprofen, Fenbufen, Pranoprofen, floctafenine, Piroxicam, Epirizole, Tiaramide hydrochloride, Zaltoprofen, Gabexate Mesilate, Camostat Mesilate, Ulinastatin, Colchicine, Probenecid, Sulfinpyrazone, Benzbromarone, Allopurinol, Brentuximab vedotin, sodium aurothiomalate, sodium hyaluronate, Atropine, Scopolamine, Morphine or a salt thereof, Pethidine, Levorphanol, Oxymorphone, Celecoxib, Etoricoxib, Valdecoxib, Loxoprofen, Auranofin, D-Penicillamine, Sulfasalazine, Mesalamine, Olsalazine, Balsalazide, Chloroquine, Leflunomide, Tacrolimus, Infliximab, Etanercept, Adalimumab, Certolizumab pegol, Golimumab, PASSTNFα, soluble TNFα receptor, TNFα binding protein, anti-TNFα antibody, Denosumab, Anakinra, soluble IL-1 receptor antibody, Tocilizumab, anti-TL-6 antibody, IL-10, Ustekinumab, Briakinumab, Secukinumab (aka AIN-457), Ixekizumab (aka LY-2439821), AMG827, Rituximab, Belimumab, Abatacept, BMS-582949, inhibiting agents for molecules involved in signal transduction, MAPK inhibiting agents, salicylic acid ointments, urea ointments, Iguratimod, Tetomilast, Belnacasan, HMPL-004, TL-8 antagonists, CXCR1-CXCR2 dual antagonists, Reparixin, CCR9 antagonists, Denileukin Diftitox, CCX025, N-{4-chloro-2-[(1-oxydopyridin-4-yl) carbonyl]phenyl}-4-(propan-2-yloxy) benzenesulfonamide, MCP-1 antagonists, Irbesartan, TNFα vaccines, ISIS-104838, Natalizumab, Vedolizumab, AJM300, TRK-170, E6007, MX-68, BMS-188667, CKD-461, Rimexolone, Cyclosporin A, Mizoribine, Gusperimus, Sirolimus, Temsirolimus, Everolimus, antlymph serums, dried sulfated immunoglobulin, erythropoietin, colony-stimulating factor, atiprimod dihydrochloride, Azathioprine, interferon α, interferon β1b, interferon β1a, Tofacitinib, Baricitinib, Carfilzomib, Ruxolitinib, Dexamethasone, Hexestrol, Thiamazole, Betamethasone, Triamcinolone Acetonide, Fluocinonide, Fluocinolone acetonide, cortisone acetate, hydrocortisone, Fluorometholone, Beclometasone, Estriol, Mycophenolate mofetil, sodium alicaforsen, selectin inhibiting agents, ELAM-1 inhibiting agents, VCAM-1 inhibiting agents, ICAM-1 inhibiting agents, V-85546, Roflumilast, Apremilast, VAS203, Reumacon, Zanolimumab, DW-1350, Zileuton, Tyk2 inhibiting agents, Synvisc (hylan G-F 20), Orthovisc, Atacicept, Blisibimod, Tizanidine, Eperisone, Afloqualone, Baclofen, diazepam, Dantrolene, vitamin D3 derivatives, vitamin D2 derivatives, Isoprenaline hydrochloride, Salbutamol sulfate, Procaterol hydrochloride, Terbutaline sulfate, Trimetoquinol hydrochloride, Tulobuterol hydrochloride, Orciprenaline sulfate, Fenoterol hydrobromide, ephedrine hydrochloride, ipratropium bromide, oxytropium bromide, Flutropium bromide, Theophylline, Aminophylline, sodium cromoglicate, Tranilast, Repirinast, Anlexanone, Ibudilast, Ketotifen, Terfenadine, Mequitazine, Azelastine, Ozagrel hydrochloride, Pranlukast hydrate, seratrodast, Ciclesonide, Chlorpheniramine maleate, Alimemazine tartrate, Clemastine fumarate, Homochlorcyclizine hydrochloride, Fexofenadine, Ketotifen fumarate, Cetirizine hydrochloride, Oxatomide, Ebastine, Epinastine hydrochloride, Loratadine, Tramadol, Promethazine, Hydroxyzine, Homochlorcyclizine, Cyproheptadine, Mequitazine, Emedastine, pseudoephedrine, Bepotastine besilate, Levocetirizine, Olopatadine hydrochloride, Mycophenolate mofetil, Daclizumab, Galiximab, Metformin hydrochloride, Visilizumab, Aminopterin, Pazopanib hydrochloride, Fezakinumab, Ruxolitinib phosphate, Ixekizumab, Guselkumab, SLx-2119, PRX-167700, Lidocaine, Tiotropium bromide, Salmeterol xinafoate, Formoterol fumarate, Fluticasone propionate, Beclometasone, Budesonide, and combination drugs of Salmeterol xinafoate and Fluticasone propionate.

[Aspect 35]A method set forth in any of [Aspect 30] through [Aspect 32], wherein an other drug is 5-fluorouracil, oxaliplatin, or irinotecan.

[Aspect 36] Use of a compound set forth in any of [Aspect 1] through [Aspect 6], or a pharmacologically acceptable salt thereof, for manufacturing a pharmaceutical composition that is a CDK7 inhibiting agent.

[Aspect 37] Use of a compound set forth in any of [Aspect 1] through [Aspect 6], or a pharmacologically acceptable salt thereof, for inhibiting CDK7.

[Aspect 38] Use of a pharmaceutical composition set forth in any of [Aspect 1] through [Aspect 6], or a pharmacologically acceptable salt thereof, for the treating or preventing of a cancer, an inflammatory disease, an allergic disease, or a chronic respiratory disease.

[Aspect 39]A use set forth in [Aspect 38], wherein the above cancer is a hematological cancer or a solid cancer.

[Aspect 40]A use set forth in [Aspect 39], wherein the hematological cancer is a selection from a group comprising multiple myeloma, chronic myelogenous leukemia, a hematological tumor, a hematologic malignancy, childhood leukemia, a childhood lymphoma, Hodgkin's disease, a lymphocytic lymphoma, a cutaneous lymphoma, acute leukemia, chronic leukemia, acute lymphoblastic leukemia, acute myelocytic leukemia, chronic myelocytic leukemia, a plasma cell neoplasm, a lymphocyte-like neoplasm, or an AIDS-related cancer.

[Aspect 41]A use set forth in [Aspect 39], wherein the solid cancer is a selection from a group comprising bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer (including squamous cell carcinoma), a fibrosarcoma, a rhabdomyosarcoma, an astrocytoma, a neuroblastoma, a glioma or schwannoma, a melanoma, a seminoma, a teratoid carcinoma, an osteosarcoma, a xeroderma pigmentosum, a keratinocytoma, a follicular carcinoma of the thyroid, or a Kaposi's sarcoma.

[Aspect 42]A use set forth in any of [Aspect 38] through [Aspect 41], wherein the inflammatory disease is an autoimmune disease.

[Aspect 43]A use set forth in [Aspect 42], wherein the autoimmune disease is rheumatoid arthritis, psoriasis, multiple sclerosis, or inflammatory bowel disease.

[Aspect 44]A use set forth in [Aspect 38], wherein the allergic disease is atopic dermatitis.

[Aspect 45]A use set forth in [Aspect 38], wherein the chronic respiratory disease is chronic obstructive pulmonary disease.

[Aspect 46]A compound or pharmacologically acceptable salt thereof set forth in any of [Aspect 1] through [Aspect 6], for use as an active ingredient in a pharmaceutical composition.

[Aspect 47]A compound or pharmacologically acceptable salt thereof set forth in [Aspect 46], for use as an active ingredient in a pharmaceutical composition for treating cancer, an inflammatory disease, an allergic disease, or a chronic respiratory disease.

[Aspect 48]A compound or pharmaceutically acceptable salt thereof set forth in [Aspect 47], wherein the above cancer is a hematological cancer or a solid cancer.

[Aspect 49]A compound or pharmaceutically acceptable salt thereof set forth in [Aspect 48], wherein the hematological cancer is a selection from a group comprising multiple myeloma, chronic myelogenous leukemia, a hematological tumor, a hematologic malignancy, childhood leukemia, a childhood lymphoma, Hodgkin's disease, a lymphocytic lymphoma, a cutaneous lymphoma, acute leukemia, chronic leukemia, acute lymphoblastic leukemia, acute myelocytic leukemia, chronic myelocytic leukemia, a plasma cell neoplasm, a lymphocyte-like neoplasm, or an AIDS-related cancer.

[Aspect 50]A compound or pharmaceutically acceptable salt thereof set forth in [Aspect 48], wherein the solid cancer is a selection from a group comprising bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer (including squamous cell carcinoma), a fibrosarcoma, a rhabdomyosarcoma, an astrocytoma, a neuroblastoma, a glioma or schwannoma, a melanoma, a seminoma, a teratoid carcinoma, an osteosarcoma, a xeroderma pigmentosum, a keratinocytoma, a follicular carcinoma of the thyroid, or a Kaposi's sarcoma.

[Aspect 51]A compound or pharmaceutically acceptable salt thereof set forth in any of [Aspect 47] through [Aspect 50], wherein the inflammatory disease is an autoimmune disease.

[Aspect 52]A compound or pharmaceutically acceptable salt thereof set forth in [Aspect 51], wherein the autoimmune disease is rheumatoid arthritis, psoriasis, multiple sclerosis, or inflammatory bowel disease.

[Aspect 53]A compound or pharmaceutically acceptable salt thereof set forth in [Aspect 47], wherein the allergic disease is atopic dermatitis.

[Aspect 54]A compound or pharmaceutically acceptable salt thereof set forth in [Aspect 47], wherein the chronic respiratory disease is chronic obstructive pulmonary disease.

Effects of the Invention

Substituted dihydropyrrolopyrazole compounds represented by general formula (I) and pharmacologically acceptable salts thereof have excellent CDK7 inhibitory activity, high selectivity for kinase inhibition, excellent safety, and excellent pharmacokinetic properties. Consequently, the compounds represented by general formula (I) and pharmacologically acceptable salts thereof are useful as drugs, especially as therapeutic and/or preventative agents for cancer, inflammatory diseases, allergic diseases, or chronic respiratory diseases.

Forms for Carrying Out the Present Invention

An embodiment according to the present invention will be explained below. Note that in this Specification, "compounds represented by general formula (I)" and the like may also be referred to as "compound (I)" and the like for convenience. The various substituent groups listed below can be selected and combined as appropriate. Note that in this specification, "dihydropyrrolopyrazole compound" may also be referred to as "dihydropyrrolopyrazole derivative."

One embodiment of the present invention is a compound represented by general formula (I), or a pharmacologically acceptable salt thereof:

[Formula 5]

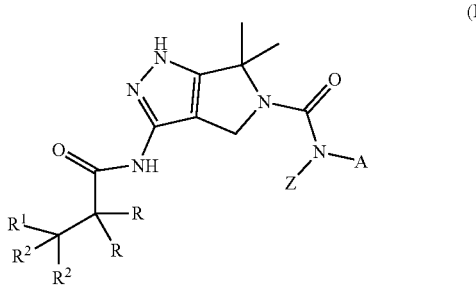

(I)

In general formula (1):
[In the formula, the two Rs each independently represents a linear or branched $C_{1-3}$ alkyl group, or a group formed by bonding them together to form a $C_{2-5}$ alkylene group,
A represents a $C_{6-10}$ aryl group (which may be a substituted $C_{6-10}$ aryl group) or a heteroaryl group (which may be a substituted heteroaryl group), Z represents a hydrogen atom or a linear or branched $C_{1-6}$ alkyl group (which may be a substituted $C_{1-6}$ alkyl group), or A and Z may be bonded to each other, with the group represented by Z—N-A forming a bicyclic fused heteroaryl group, which may be substituted, and
$R^1$, $R^2$, and $R^3$ each independently represents a linear or branched $C_{1-4}$ alkyl group that may be substituted.]

The term "linear or branched $C_{1-6}$ alkyl group" in the present Specification means a linear or branched alkyl group with 1-6 carbon atoms. The linear or branched $C_{1-6}$ alkyl group may be, for example, a $C_{1-6}$ alkyl group such as a methyl group, an ethyl group, a propyl group, an isopropyl group, a butyl group, an isobutyl group, a sec-butyl group, a tert-butyl group, a pentyl group, an isopentyl group, a neopentyl group, tert-pentyl group, a 1-ethylpropyl group, a 1-methylbutyl group, a 2-methylbutyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1,2-dimethylbutyl group, a 1,3-dimethylbutyl group, or a 2,3-dimethylbutyl group. Preferred "linear or branched $C_{1-6}$ alkyl groups" are methyl, ethyl, propyl, isopropyl, butyl, isobutyl, sec-butyl, and tert-butyl groups. Similarly, the term "linear or branched $C_{1-3}$ alkyl group" refers to a linear or branched alkyl group with 1-3 carbons, and the term "linear or branched $C_{1-4}$ alkyl group" refers to a linear or branched alkyl group with 1-4 carbons.

The "$C_{2-5}$ alkylene group" in the present Specification includes a 1,2-ethylene group, a 1,2-propylene group, a 1,3-propylene group, a 1,2-butylene group, a 1,3-butylene group, a 1,4-butylene group, a 2,3-butylene group, a 1,2-pentylene group, a 1,3-pentylene group, a 1,4-pentylene group, a 1,5-pentylene group, a 2,3-pentylene group, and a 2,4-pentylene group. That is, a group in which two Rs are bonded to each other to form a $C_{2-5}$ alkylene group means a divalent group consisting of a $C_{2-5}$ alkyl group corresponding to a carbon number of 2-5, from the $C_{1-6}$ alkyl groups described above, with one hydrogen atom removed.

The term "$C_{6-10}$ aryl group" in the present specification means an aryl group with 6-10 carbons. The $C_{6-10}$ aryl group includes, for example, phenyl and naphthyl groups.

The "heteroaryl group" in the present specification corresponds to an aromatic heterocyclic group, among the heterocyclic groups described below, and in particular, the "bicyclic fused heteroaryl group" corresponds to a bicyclic aromatic heterocyclic group.

In the present Specification, the term "which may be substituted" in the explanations of A, Z, $R^1$, $R^2$, $R^3$, and the like, means that such groups include those that are unsubstituted and those that are substituted with one or more of the substituents A, described below.

The aforementioned substituent A means a monovalent group, which may be, for example, a linear or branched $C_{1-6}$ alkyl group, a $C_{3-6}$ cycloalkyl group, a linear or branched $C_{2-6}$ alkenyl group, a $C_{3-6}$ cycloalkenyl group, a linear or branched $C_{2-6}$ alkynyl group, a linear or branched $C_{1-6}$ alkoxy group, a $C_{3-6}$ cycloalkoxy group, a halogen atom, a hydroxyl group, a cyano group, an oxo group (═O), an amino group, a nitro group, a carboxy group (—COOH), a carbamoyl group (—CONH₂), a $C_{6-10}$ aryl group, or and a heterocyclic group. If the substituent is an amino group or a carboxy group, it may be in the form of a salt thereof. Preferably the substituent A is a linear or branched $C_1$. 6 alkyl group or a halogen atom.

The term "$C_{3-6}$ cycloalkyl group" in the present specification means a cyclic alkyl group with 3-6 carbons. $C_{3-6}$ cycloalkyl groups include, for example, monocyclic rings such as cyclopropyl, cyclobutyl, cyclopentyl, and cyclohexyl groups; fused rings such as bicyclo[3.1.0]hexyl groups; and spiro rings such as spiro[2.3]hexyl groups. The substituent referenced above is preferably a cyclopropyl group or a cyclobutyl group.

The term "linear or branched $C_{2-6}$ alkenyl group" in the present Specification means a linear or branched alkenyl group with 2-6 carbon atoms. The linear or branched $C_{2-6}$ alkenyl groups may be, for example, a vinyl group, a propene-1-yl group, a propene-2-yl group, a 1-butenyl group, a 2-butenyl group, a 3-butenyl group, a 1-methyl-1-propenyl group, a 2-methyl-1-propenyl group, a 1-pentenyl group, a 2-pentenyl group, a 3-pentenyl group, a 4-pentenyl group, a 5-pentenyl group, a 1-methyl-1-butenyl group, a 2-methyl-1-butenyl group, a 3-methyl-1-butenyl group, a 4-methyl-1-butenyl group, a 1-methyl-2-butenyl group, a 2-methyl-2-butenyl group, a 3-methyl-2-butenyl group, a 4-methyl-2-butenyl group 1-methyl-2-butenyl group, a 1-methyl-3-butenyl group, a 2-methyl-3-butenyl group, a 3-methyl-3-butenyl group, a 4-methyl-3-butenyl group, a 1,2-dimethyl-1-propenyl group, a 1-hexenyl group, a 2-hexenyl group, a 3-hexenyl group, a 4-hexenyl group, a 5-hexenyl group, a 6-hexenyl group, or an alkenyl group such as a structural isomer thereof.

The term "$C_{3-6}$ cycloalkenyl group" in the present specification means a cycloalkenyl group with 3-6 carbons. $C_{3-6}$ cycloalkenyl groups include, for example, cyclopropenyl, cyclobutenyl, cyclopentenyl, and cyclohexenyl groups.

The term "linear or branched $C_{2-6}$ alkynyl group" in the present specification means a linear or branched alkynyl group with 2-6 carbon atoms. Linear or branched $C_{2-6}$ alkynyl groups include, for example, ethynyl, propargyl, butynyl, penthynyl, and hexynyl groups.

The term "linear or branched $C_{1-6}$ alkoxy group" in the present specification means a group consisting of an oxy group (—O—) and a linear or branched $C_{1-6}$ alkyl group attached to said oxy group. $C_{1-6}$ alkoxy groups include, for example, methoxy, ethoxy, propyloxy, isopropyloxy, butoxy, pentyloxy, and hexyloxy groups.

The term "$C_{3-6}$ cycloalkoxy group" in the present specification means a group consisting of an oxy group (—O—) and a linear or branched $C_{3-6}$ cycloalkyl group attached to said oxy group. $C_{3-6}$ cycloalkoxy groups include, for example, cyclopropenyloxy, cyclobutenyloxy, cyclopentenyloxy, and cyclohexenyloxy groups.

"Halogen atom" in the present Specification means a fluorine atom, a chlorine atom, a bromine atom, or an iodine atom.

The term "heterocyclic group" in the present specification means a cyclic group having at least one nitrogen atom, oxygen atom, or sulfur atom, and may be an aromatic heterocyclic group (also referred to as a "heteroaryl group") or may be a non-aromatic heterocyclic group. The heterocyclic group may be monocyclic or bicyclic. A heterocyclic group as a substituent preferably is monocyclic. Monocyclic aromatic heterocyclic groups include, for example, pyridine, pyrimidine, pyridazine, pyrazine, triazine, pyrrole, imidazole, pyrazole, indazole, furan, thiophene, thiazole, isothiazole, oxazole, isoxazole, and oxadiazole groups. Monocyclic non-aromatic heterocyclic groups include, for example, pyrrolidinyl, piperidinyl, piperazinyl, morpholinyl, and thiomorpholinyl groups. Bicyclic aromatic heterocyclic groups (also termed "bicyclic fused heteroaryl groups") include, for example, indole, benzofuran, benzothiophene, benzothiazole, benzoxazole, pyridoindole, and quinoxaline groups.

If the applicable group has two or more substituent groups A, the two substituent groups A may be bonded to each other to form a cyclic structure. A case wherein two substituent groups A are bonded to each other to form a cyclic structure may be, for example, a cyclopropyl group, a methylenedioxy group, or an oxyethylene group. Specifically, when a methylenedioxy group is bonded to the benzene ring, the entirety becomes a 1,3-benzodioxole group, and when an oxyethylene group is bonded to the benzene ring, the entirety becomes a 2,3-dihydrobenzofuranyl group.

If the substituent group A is a halogen atom, the "substituted linear or branched $C_{1-6}$ alkyl group" may be, for example, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a pentafluoroethyl group, a 2,2-dichloroethyl group, a 2,2,2-trichloroethyl group, a 1-fluoropropyl group, a 2-fluoropropyl group, a 3-fluoropropyl group, a 3,3,3-trifluoropropyl group, a perfluoropropyl group, a 1-fluoromethyl ethyl group, a 1-difluoromethyl ethyl group, a 1-trifluoromethyl ethyl group, a 1-fluoro-1-methylethyl group, a 4-fluorobutyl group, a perfluorobutyl group, a 5-fluoropentyl group, a perfluoropentyl group, a 6-fluorohexyl group, or a perfluorohexyl group.

If the substituent group A is a $C_{6-10}$ aryl group, the "substituted linear or branched $C_{1-6}$ alkyl group" may be, for example, an alkyl group with an aryl group, with a total carbon number of 7-11 (also called a $C_{7-11}$ aralkyl group), and specific examples thereof include benzyl groups, phenylethyl groups, and naphthylmethyl groups.

The substituent group A may be further substituted with substituent group B such as a halogen atom, a hydroxyl group, an amino group, a cyano group, an oxo group (=O), a linear or branched $C_{1-6}$ alkyl group, a $C_{1-6}$ alkoxy group, a $C_{6-10}$ aryl group, a heterocyclic group, or the like. Such a substituent group (That is, a substituent group A substituted with a substituent group B) may be, for example, an alkylamino group, an N-mono $C_{1-6}$ alkylcarbamoyl group, an N,N-di $C_{1-6}$ alkylcarbamoyl group (where the two alkyl groups may be need not be identical), or a $C_{1-6}$ alkanoyloxy group (—OCOR$^4$), [where R$^4$ is a linear or branched $C_{1-5}$ alkyl group]). Typically, a methyl group substituted with a hydroxyl group and an oxo group is referred to as a carboxy group (—COOH). Typically, an amino group substituted with a hydroxyl group and an oxo group is referred to as a carbamoyl group (—CONH$_2$).

"Alkylamino group" in the present specification means an amino group substituted with one or more groups selected independently from the linear or branched $C_{1-6}$ alkyl groups and $C_{3-6}$ cycloalkyl groups described above. $C_{1-6}$ alkylamino groups include, for example, methylamino, ethylamino, propylamino, isopropylamino, cyclopropylamino, butylamino, cyclobutylamino, pentylamino, cyclopentylamino, hexylamino, cyclohexylamino, dimethylamino, diethylamino, ethyl (methyl) amino, isopropyl (methyl) amino, and cyclopropyl (methyl) amino groups.

The compound according to the present embodiment may be represented by any of the chemical formulas of general formula (II), general formula (III), or general formula (IV).

[Formula 6]

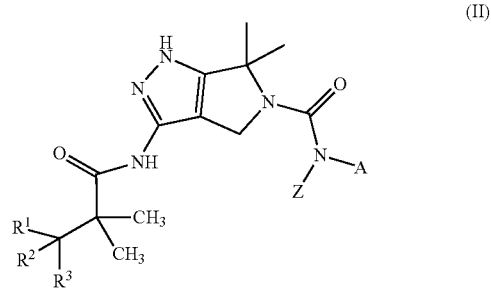

(II)

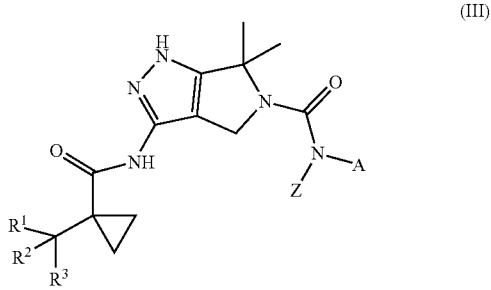

(III)

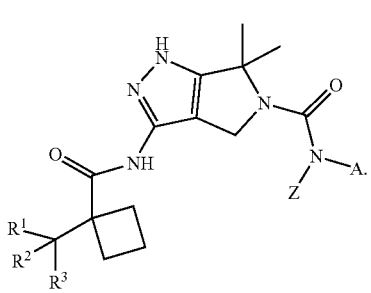

(IV)

In general formula (II), general formula (III), and general formula (IV), $R^1$, $R^2$, $R^3$, and A are the same as defined in general formula (I).

In general formula (I), the two Rs may each independently be a linear or branched $C_{1-3}$ alkyl group, or a group wherein they are bonded together to together to form a $C_{2-5}$ alkylene group.

In general formula (I), general formula (II), general formula (III), and general formula (IV), $R^1$, $R^2$, and $R^3$ may each independently be a linear or branched $C_{1-4}$ alkyl group that may be substituted.

In general formula (I), general formula (II), general formula (III), and general formula (IV), A may be a $C_{6-10}$ aryl group (which may be substituted), or a heteroaryl group (which may be substituted).

In a preferred form of the compound that is represented by general formula (I), the compound is one wherein the two Rs each independently represents a linear or branched $C_{1-3}$ alkyl group, or a group formed by bonding them together to form a $C_{2-3}$ alkylene group.

Moreover, in preferred forms of the compounds represented by general formula (I), general formula (II), general formula (III), or general formula (IV), the compound is one wherein, in each general formula, A represents a phenyl group that may be substituted, and $R^1$, $R^2$, and $R^3$ each independently represents a methyl group or an ethyl group.

Preferably the compound in the present embodiment is a compound represented by general formula (IV), and more preferably a compound in which $R^1$, $R^2$, and $R^3$ in the formula is each a $C_{1-3}$ alkyl group, Z is a hydrogen atom, and A is a phenyl group or benzofuranyl group, which may be substituted. The above phenyl group or benzofuranyl group may be substituted with 1-3 groups independently selected from a set consisting of halogen atoms and $C_{1-3}$ alkyl groups.

For the compound (I), compounds selected from the following groups of compounds are preferred:
3-(1-(tert-butyl) cyclobutane-1-carboxamide)-N-(2-fluorophenyl)-6,6-dimethyl-4,6-dihydropyrrolo [3,4-c]pyrazole-5 (1H)-carboxamide,
3-(1-(tert-butyl) cyclobutane-1-carboxamide)-N-(o-tolyl)-6,6-dimethyl-4,6-dihydropyrrolo [3,4-c]pyrazole-5 (1H)-carboxamide,
3-(1-(tert-butyl) cyclobutane-1-carboxamide)-N-(2-chloro-6-methylphenyl)-6,6-dimethyl-4,6-dihydropyrrolo [3,4-c] pyrazole-5 (1H)-carboxamide,
3-(1-(tert-butyl) cyclobutane-1-carboxamide)-N-(5-fluoro-2-methylphenyl)-6,6-dimethyl-4,6-dihydropyrrolo [3,4-c] pyrazole-5 (1H)-carboxamide,
3-(1-(tert-butyl) cyclobutane-1-carboxamide)-N-(2,5-dimethylphenyl)-6,6-dimethyl-4,6-dihydropyrrolo [3,4-c] pyrazole-5 (1H)-carboxamide,
3-(1-(tert-butyl) cyclobutane-1-carboxamide)-N-(2,6-dimethylchlorophenyl)-6,6-dimethyl-4,6-dihydropyrrolo [3,4-c]pyrazole-5 (1H)-carboxamide,
3-(1-(tert-butyl) cyclobutane-1-carboxamide)-N-(2-chloro-6-fluorophenyl)-6,6-dimethyl-4,6-dihydropyrrolo [3,4-c] pyrazole-5 (1H)-carboxamide,
N-(2-bromo-6-methylphenyl)-3-(1-(tert-butyl) cyclobutane-1-carboxamide)-6,6-dimethyl-4,6-dihydropyrrolo [3,4-c] pyrazole-5 (1H)-carboxamide,
3-(1-(tert-butyl) cyclobutane-1-carboxamide)-N-(2-fluoro-3,6-dimethylphenyl)-6,6-dimethyl-4,6-dihydropyrrolo [3,4-c]pyrazole-5 (1H)-carboxamide,
3-(1-(tert-butyl) cyclobutane-1-carboxamide)-N-(6-fluorobenzofuran-7-yl)-6,6-dimethyl-4,6-dihydropyrrolo [3,4-c]pyrazole-5 (1H)-carboxamide, and
3-(1-(tert-butyl) cyclobutane-1-carboxamide)-N-(2-chloro-6-fluorobenzofuran-7-yl)-6,6-dimethyl-4,6-dihydropyrrolo [3,4-c]pyrazole-5 (1H)-carboxamide.

The compound (I) or pharmacologically acceptable salt thereof may be a single optical isomer, or a mixture of multiple optical isomers.

If geometric or rotational isomers are present in compound (I), these isomers are also included in the present invention. If tautomers exist in the compound of the present embodiment, these tautomers are also included in the present invention.

There are no particular limitations on the "pharmacologically acceptable salts" in the present embodiment insofar as they are salts that are acceptable as a medicine, and include, for example: salts with inorganic acids such as hydrochloric acid, hydrobromic acid, hydriodic acid, nitric acid, sulfuric acid, phosphoric acid, and the like; salts with organic carboxylic acids such as acetic acid, fumaric acid, maleic acid, succinic acid, citric acid, tartaric acid, adipic acid, lactic acid, trifluoroacetic acid, and the like; salts with organic sulfonic acids such as methanesulfonic acid, trifluoromethanesulfonic acid, benzenesulfonic acid, p-toluenesulfonic acid, and naphthalenesulfonic acid, and the like; salts with alkali metals such as lithium, sodium, and potassium, and the like; salts with alkaline earth metals such as calcium and magnesium, and the like; and quaternary ammonium salts with ammonia, morpholine, glucosamine, ethylenediamine, guanidine, diethylamine, triethylamine, dicyclohexylamine, diethanolamine, piperazine, and the like.

The compound (I) or pharmacologically acceptable salt thereof can form a hydrate or a solvate; each of these, and mixtures thereof, are included in the present invention.

The compound (I) may also contain atomic isotopes in non-natural ratios in one or more of its constituent atoms. Atomic isotopes include, for example, deuterium (H), tritium ($^3$H), carbon-11 ($^{11}$C), carbon-14 ($^{14}$C), fluorine-18 ($^{18}$F), sulfur-35 ($^{35}$S), or iodine-125 ($^{125}$I). These compounds are useful as therapeutic or preventative agents, or research reagents such as, for example, assay reagents, and diagnostic agents, such as, for example, in vivo imaging agents. All isotopic variants of compound (I) are included in the present invention, regardless of whether or not they are radioactive.

The compound (I) or pharmacologically acceptable salt thereof may be used as a pharmaceutical composition by adding, as necessary, pharmacologically acceptable carriers for, for example, excipients, lubricants, binders, disintegrants, coating agents, stabilizing agents, isotonic agents, buffering agents, pH adjusting agents, solubilizing agents, thickening agents, preservatives, antioxidants, sweeteners, colorants, and flavors. Pharmaceutical compositions can be prepared through methods known to those skilled in the art and in accordance with the objective.

In a pharmaceutical composition, the content of compound (I) or pharmacologically acceptable salt thereof can be adjusted as appropriate.

The pharmaceutical composition may be made in the form of a tablet, a capsule, a granulated material, a spray or other form for oral administration, an injection (which may be, for example, intravenous, subcutaneous, intramuscular, or intraperitoneal), eye drops, nasal drops, suppositories, ointments, lotions, creams, gels, sprays, pastes, inhalants, transdermal absorption preparations or some other parenteral dosage forms as described in the General Rules for Preparations of the Japanese Pharmacopoeia, Sixteenth Edition.

Excipients include, for example, lactose, mannitol, starch, crystalline cellulose, light anhydrous silicic acid, calcium carbonate, and calcium hydrogen phosphate, and lubricants include, for example, stearic acid, magnesium stearate, and talc. Binders include, for example, starch, hydroxypropyl cellulose, hydroxypropyl methyl cellulose, and polyvinylpyrrolidone, and disintegrants include, for example, carboxymethyl cellulose, low-substituted hydroxypropyl methyl cellulose, and calcium citrate. Coating agents include, for example, hydroxypropyl methylcellulose, macrogol, and silicone resins, and stabilizers include, for example, ethyl paraoxybenzoate and benzyl alcohol.

Isotonic agents include, for example, glycerin, propylene glycol, sodium chloride, potassium chloride, sorbitol, mannitol, and the like; buffer agents include boric acid, borates, phosphoric acid, phosphates, citric acid, citrates, acetic acid, acetates, F-aminocaproic acid, trometamol, and the like; and pH adjusting agents include, for example, hydrochloric acid, citric acid, phosphoric acid, glacial acetic acid, sodium hydroxide, potassium hydroxide, sodium carbonate, sodium bicarbonate, and the like. Solubilizing agents include, for example, polysorbate 80, polyoxyethylene-hardened castor oil 60, MACROGOL 4000, purified soy lecithin, polyoxyethylene (160) polyoxypropylene (30) glycol, and the like, and thickening agents include, for example, cellulosic polymers such as hydroxypropyl methylcellulose and hydroxypropyl cellulose, along with polyvinyl alcohol, polyvinylpyrrolidone, and the like. Stabilizing agents include, for example, edetic acid, sodium edetate, and the like, and preservatives include, for example, sorbic acid, potassium sorbate, benzalkonium chloride, benzethonium chloride, methyl parahydroxybenzoate, propyl parahydroxybenzoate, chlorobutanol, and the like.

Ingredients that may be included in pharmaceutical compositions for transdermal administration, such as ointments, lotions, creams, gels, and sprays, may include, for example: absorption enhancing agents such as lauryl alcohol, myristyl alcohol, ethylene glycol salicylate, pyrothiodecane, and the like; fatty acid esters such as diisopropyl adipate, isopropyl myristate, cetyl lactate, myristyl lactate, isopropyl palmitate, diethyl sebacate, hexyl laurate, cetyl isooctanoate, and the like; aliphatic alcohols such as cetyl alcohol, stearyl alcohol, oleyl alcohol, hexadecyl alcohol, behenyl alcohol, and the like; glycols such as propylene glycol, propylene diol, polyethylene glycol, dipropylene glycol, and the like; and surfactants such as sorbitan fatty acid esters, glycerin fatty acid esters, polyoxyethylene sorbitan fatty acid esters, polyoxyethylene glycerin fatty acid esters, polyethylene glycol fatty acid esters, polyoxyethylene alkyl ethers, polyoxyethylene castor oil, polyoxyethylene hardened castor oil, and the like.

The dosage of compound (I) or the pharmacologically acceptable salt thereof may be modified according to symptoms, age, dosage form, and the like. For example, when administered orally, normally 0.01 to 2000 mg per day, and preferably 1 to 500 mg per day, may be administered, either as a single dose or divided into several doses.

For ointments, lotions, creams, or gels, normally a concentration of 0.0001% (w/v) to 10% (w/v), and preferably 0.01% (w/v) to 5% (w/v), can be administered a single time, or divided into multiple administrations.

A method for producing the compound (I) or pharmacologically acceptable salt thereof will be explained next. Note that the compound or pharmacologically acceptable salt thereof is not limited to a compound or pharmacologically acceptable salt produced through the production methods set forth below.

If, in the production methods set forth below, there are partial structures (such as hydroxy groups, amino groups, carbonyl groups, carboxyl groups, amide groups, or thiol groups) in the compound that may inhibit the desired reaction or cause side reactions, protective groups may be introduced for those partial structures, with the protective groups removed thereafter, to produce the desired result.

The reactions for introducing and removing the protective groups can be carried out in accordance with methods commonly used in organic synthetic chemistry (such as a method described in Protective Groups in Organic Synthesis, Fourth Edition, by T. W. Greene and P. G. M. Wuts, John Wiley & Sons Inc. (2006), or the like).

In the below, as methods for producing the compound (I), methods will be described for producing the compound (I) with a compound (1) as a starting material (Production Methods 1 through 4 for Compound (I)). Note that a method for producing this compound (1) will be described below.

<Production Method for Compound (I)>

In this method, a compound (2), produced through reacting an acylating agent with compound (1), and an amine compound (3) are reacted to produce a compound (4), followed by production of the compound (I). In this method, R, $R^1$, $R^2$, $R^3$, A, and Z are identical to the definitions of general formula (I). The $P^1$ group represents the protective group of the amino group, and X represents the extraction group. Note that while, for convenience, the method will be explained with the chemical structure of compound (1) shown with a $P^1$ group substituted at the 1-position of the 4,6-dihydropyrrolo [3,4-c]pyrazole skeleton, compound (1) may instead be a compound having a chemical structure corresponding to a tautomer in which the $P^1$ group is substituted at the 2-position of the 4,6-dihydropyrrolo [3,4-c]pyrazole skeleton.

[Formula 7]

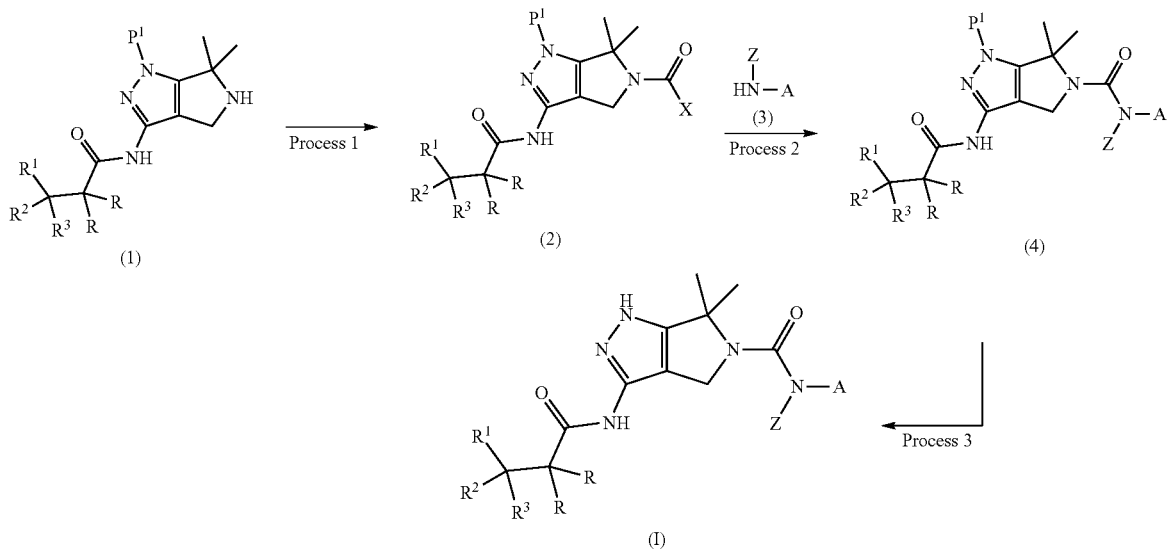

The P¹ group can be any substituent group known to those skilled in the art as a protective group for amino groups. The P¹ group may be, for example, a $C_{7-11}$ aralkyl group (which may be substituted), such as a benzyl group, a p-methoxyphenylmethyl group, an o-nitrophenylmethyl group, or the like; a $C_{1-6}$ alkyl carbonyl group (which may be substituted), such as an acetyl group, a trifluoroacetyl group, or the like; a $C_{6-10}$ arylcarbonyl group (which may be substituted), such as a benzoyl group, or the like; a $C_{1-6}$ alkoxycarbonyl group (which may be substituted), such as a methoxycarbonyl group, an ethoxycarbonyl group, a Boc group (tert-butoxycarbonyl group), a Cbz group (benzyloxycarbonyl group), an Fmoc group (fluorenylmethyloxycarbonyl group), a Teoc group (trimethylsilylethyl oxycarbonyl group), or the like; an alkenyloxycarbonyl group, such as an Alloc group (allyloxycarbonyl group), or the like; an alkylsulfonyl group, such as a methanesulfonyl group, or the like; or a $C_{6-10}$ arylsulfonyl group (which may be substituted), such as a p-toluenesulfonyl group, or the like.

The X group can be any substituent group known to those skilled in the art as an extraction group for amino groups. The X group may be, for example: a halogen atom such as a fluorine atom, a chlorine atom, a bromine atom, an iodine atom, or the like; an imidazolyl group; an aminooxy group such as a succinyl-N-oxy group, a benzotriazolyl-N-oxy group, or the like; a $C_{1-6}$ alkylcarbonyloxy groups (which may be substituted), such as a pivaloyloxy group; or a $C_{6-10}$ arylcarbonyloxy group (which may be substituted), such as a benzoyloxy group. X may be a hydroxyl group instead.

(Process 1) Process 1 is a process for reacting compound (1) with an acylating agent to produce compound (2).

The acylating agent uses, for example, phosgene, diphosgene, triphosgene, carbonyl diimidazole (CDI), N,N'-disuccinimidyl carbonate, a carbonate ester, or the like.

The amount of acylating agent used is preferably 0.4 to 3.0 moles, and more preferably 0.7 to 1.5 moles, per 1 mole of compound (1).

In process 1, the reaction may be carried out in a solvent or without a solvent. There is no particular limitation on the solvent, insofar as it does not have an effect on the reaction, and preferably it is an organic solvent. The organic solvent may be, for example, dichloromethane, 1,2-dichloroethane, diethyl ether, 1,2-dimethoxyethane, tetrahydrofuran (THF), N,N-dimethylformamide (DMF), or dimethyl sulfoxide (DMSO).

In Process 1, a base may further be added to accelerate the reaction. The base may be an organic amine such as, for example, triethylamine (TEA), diisopropylethylamine (DIPEA), 1,5-diazabicyclo [4.3.0]nonene (DBN), 1,8-diazabicyclo [5.4.0]undecene (DBU), pyridine, 4-dimethylaminopyridine (DMAP), or the like.

The amount of the base added is preferably 1 to 10 moles, and more preferably 3 to 6 moles, per 1 mole of compound (1).

The reaction temperature in Process 1 can be set as appropriate by a person skilled in the art. Usually the reaction temperature is between −100 and 0° C., and preferably between −80 and −60° C.

(Process 2) Process 2 is a process for reacting compound (2) with an amine compound (3) to produce a compound (4). The amine compound (3) may be a primary or secondary amine in which A and Z satisfy the definitions in general formula (I), and may be a commercially available amine or a synthesized amine.

The amount of amine compound (3) used is preferably 1 to 20 moles, and more preferably 2 to 5 moles, per 1 mole of compound (2). The amine compound (3) and compound (2) may be dissolved in an organic solvent and added to the reaction solution.

In Process 2, the reaction may be carried out in a solvent or without a solvent. There is no particular limitation on the solvent, insofar as it does not have an effect on the reaction, and preferably it is an organic solvent. The organic solvent may be, for example, dichloromethane, 1,2-dichloroethane, 1,4-dioxane, 1,2-dimethoxyethane, tetrahydrofuran (THF), N,N-dimethylformamide (DMF), or dimethyl sulfoxide (DMSO).

In Process 2, a base may further be added to accelerate the reaction. The base may be an organic amine such as, for example, triethylamine (TEA), diisopropylethylamine (DIPEA), 1,5-diazabicyclo [4.3.0]nonene (DBN), 1,8-diazabicyclo [5.4.0]undecene (DBU), pyridine, 4-dimethylaminopyridine (DMAP), or the like; or an inorganic base such as potassium carbonate, sodium carbonate, or the like.

The amount of the base added is preferably 1 to 20 moles, and more preferably 2 to 5 moles, per 1 mole of compound (1).

The reaction temperature in Process 2 can be set as appropriate by a person skilled in the art. Usually the reaction temperature is between 0 and 160° C., and preferably between 25 and 120° C.

(Process 3) Process 3 is a process for removing the $P^1$ group from compound (4) to produce the compound (I).

The reaction conditions of Process 3 can be selected by a person skilled in the art depending on the type of $P^1$ group that is used. For example, if the $P^1$ group is a $C_{7-11}$ aralkyl group (which may be substituted), the $P^1$ group may be removed through hydrolysis, or through use of protic acid or Lewis acid. If the $P^1$ group is a $C_{1-6}$ alkylcarbonyl group (which may be substituted), a $C_{6-10}$ arylcarbonyl group (which may be substituted), or a $C_{6-10}$ arylsulfonyl group (which may be substituted), the $P^1$ group may be removed through the use of protic acid or Lewis acid. If the $P^1$ group is a Boc group, it may be through processing with protic acid or Lewis acid; if the $P^1$ group is a Cbz group, it may be through hydrogenolysing or processing with a base; or if the $P^1$ group is a Teoc group, it may be through the use of a reagent that produces fluoride ions such as tetrabutylammonium fluoride. If the $P^1$ group is a $C_{1-6}$ alkoxycarbonyl group (which may be substituted), such as a methoxycarbonyl group or an ethoxycarbonyl group, the $P^1$ group may be removed by heating in the presence of an organic amine such as triethylamine (TEA), diisopropylethylamine (DIPEA), 2-aminoethanol, N,N-dimethyl ethane-1,2-diamine, or the like, or an inorganic base such as potassium carbonate or sodium carbonate.

The compound (I) produced by Process 3 can be converted to a pharmacologically acceptable salt thereof through a method known to those skilled in the art.

<Production Method 1 for Compound (4a)>

In this method, compound (1) is reacted with an isocyanate compound (5) to produce a compound (4a), after which the compound (I) is produced in the same manner as in Process 3 above. The compound (4a) corresponds to a case where the Z group is a hydrogen atom in general formula (4). Process 3 is as described above. This method is well suited when an isocyanate compound (5) is used. In this method, R, $R^1$, $R^2$, $R^3$, $P^1$, and A are identical to the definitions in the method for producing the compound (I), above.

[Formula 8]

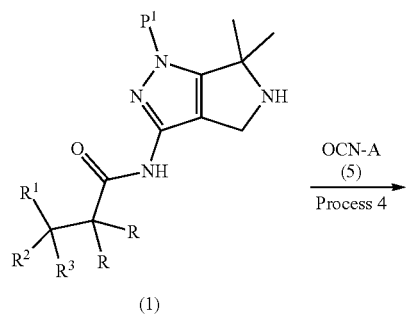

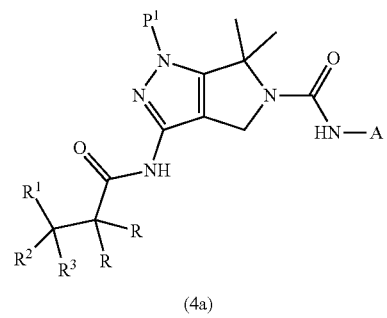

(Process 4) Process 4 is a process for reacting the compound (1) with the isocyanate compound (5) to produce the compound (4a). Insofar as A is an isocyanate that satisfies the definition in general formula (1), the isocyanate compound (5) may be either a commercially available isocyanate or a synthesized isocyanate.

The amount of the compound (5) used is preferably 1 to 10 moles, and more preferably 1 to 3 moles, per 1 mole of compound (1). Compound (5) may be dissolved in an organic solvent and added to the reaction solution.

In Process 4, the reaction may be carried out in a solvent or without a solvent. There is no particular limitation on the solvent, insofar as it does not have an effect on the reaction, and preferably it is an organic solvent. The organic solvent may be, for example, dichloromethane, 1,2-dichloroethane, 1,4-dioxane, 1,2-dimethoxyethane, tetrahydrofuran (THF), N,N-dimethylformamide (DMF), or dimethyl sulfoxide (DMSO).

The reaction temperature in Process 4 can be set as appropriate by a person skilled in the art. Usually the reaction temperature is between −20 and 100° C., and preferably between 0 and 30° C.

<Production Method 2 for Compound (4a)>

In this method, compound (1) is reacted with an isocyanate compound (5) that is obtained through conversion of a carboxylic acid compound (6), to produce a compound (4a), after which the compound (I) is produced in the same manner as in Process 3 above. Note that, in this method, processes 5 and 6 may be carried out continuously without isolating the isocyanate compound (5). Insofar as A is a carboxylic acid that satisfies the definition in general formula (1), the carboxylic acid compound (6) may be either a commercially available carboxylic acid or a synthesized carboxylic acid. In this method, R, $R^1$, $R^2$, $R^3$, $P^1$, and A are identical to the definitions in the method for producing the compound (I), above.

[Formula 9]

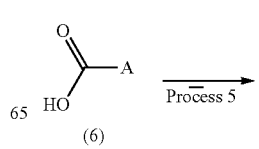

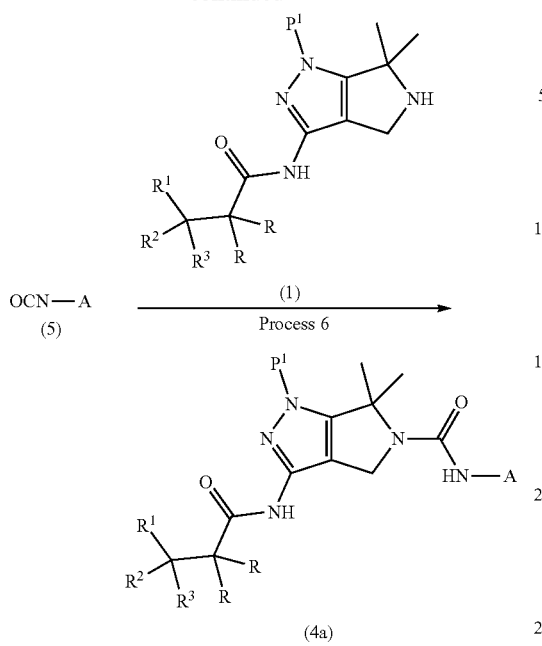

(Process 5) Process 5 is a process for reacting the isocyanate compound (5) with diphenylphosphoryl azide and a base (Curtius rearrangement) to produce the isocyanate compound (5) based on a method described in, for example, Journal of the American Chemical Society, 94 (1972), pp. 6203-6205.

In Process 5, the reaction may be carried out in a solvent or without a solvent. Insofar as the solvent does not affect the reaction, there is no particular limitation on the solvent, which may be, such, for example, an aromatic hydrocarbon such as toluene, xylene, or the like; or an amide such as N,N-dimethylformamide (DMF), N,N-dimethylacetamide, 1-methyl-2-pyrrolidone, or the like. Toluene is preferred.

The base may be, for example, an organic amine such as triethylamine (TEA), diisopropylethylamine (DIPEA), or the like.

(Process 6) Process 6 is a process for reacting the compound (1) with the isocyanate compound (5) to produce the compound (4a). Process 6 is carried out using the same method as Process 4.

<Production Method 3 for Compound (4a)>

In this method, compound (1) is reacted with an isocyanate compound (5) that is obtained through conversion of an amide compound (7), to produce a compound (4a), after which the compound (I) is produced in the same manner as in Process 3 above. Note that, in this method, processes 7 and 8 may be carried out continuously without isolating the compound (5). Insofar as A is a primary amide that satisfies the definition in general formula (1), the amide compound (7) may be either a commercially available amide or a synthesized amide. This method is well suited when an amide compound (7) is used. In this method, R, R¹, R², R³, P¹, and A are identical to the definitions in the method for producing the compound (I), above.

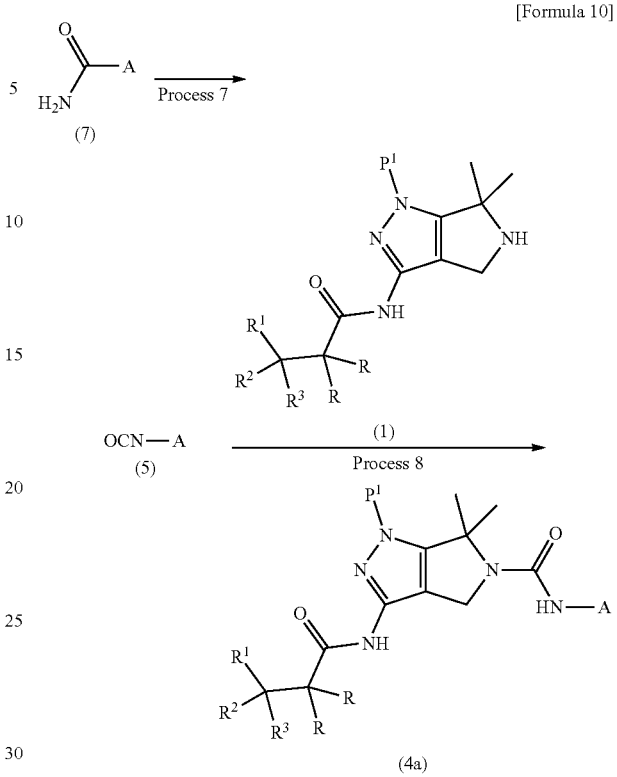

(Process 7) Process 7 is a process for reacting compound (7) with an oxidizing agent (Hoffmann rearrangement) to produce an isocyanate compound (5), based on the method described in Organic Synthesis, 66 (1988), pp. 132-137, for example.

In Process 7, the reaction may be carried out in a solvent or without a solvent. Insofar as the solvent does not affect the reaction, there is no particular limitation on the solvent, which may be, for example: an aromatic hydrocarbon such as toluene, xylene, or the like; an amide such as N,N-dimethylformamide (DMF), N,N-dimethylacetamide, 1-methyl-2-pyrrolidone, or the like; a halogenated aliphatic hydrocarbon such as dichloromethane, 1,2-dichloroethane, or the like; a halogenated aromatic hydrocarbon such as chlorobenzene, 1,2-dichlorobenzene, or the like; or a nitrile such as acetonitrile, propionitrile, or the like. Toluene is preferred.

A base may be added to the reaction in Process 7. The base may be, for example: an organic amine such as triethylamine (TEA) diisopropylethylamine (DIPEA), or the like; or a pyridine such as pyridine, 2,6-lutidine, 4-picoline, or the like. Pyridine is preferred.

The oxidizing agent may be a high-valent iodine compound such as [bis(acetoxy)iodo]benzene, [bis(trifluoroacetoxy)iodo]benzene, or iodosylbenzene, or the like, where [bis(trifluoroacetoxy)iodo]benzene is preferred.

The compound (4a) produced by the above production methods 1 through 3 for compound (4a) may be converted to the compound (4) (wherein the Z group is not a hydrogen atom) by a reaction that is known to those skilled in the art. Compound (4a) may instead be converted to a compound (Ia) and then converted to the compound (I) (wherein the Z group is not a hydrogen atom). The compound (Ia) corresponds to a case where the Z group is a hydrogen atom in general formula (I). For example, in Process 4, 6 or 8, the mixture after the reaction may be reacted with an alkylating agent Z—X (wherein Z is the same as that which is defined in general formula (I) and X is an extraction group).

(Process 8) Process 8 is a process for reacting the compound (1) with the isocyanate compound (5) to produce the compound (4a). Process 8 is carried out using the same method as Process 4.

<Production Method for Compound (1)>

Compound (1) may be produced, for example, through the method below, using compound (8) as a starting material. Compound (8) may be produced, for example, with reference to WO2007/72153 or through processes 11 through 15, below.

[Formula 11]

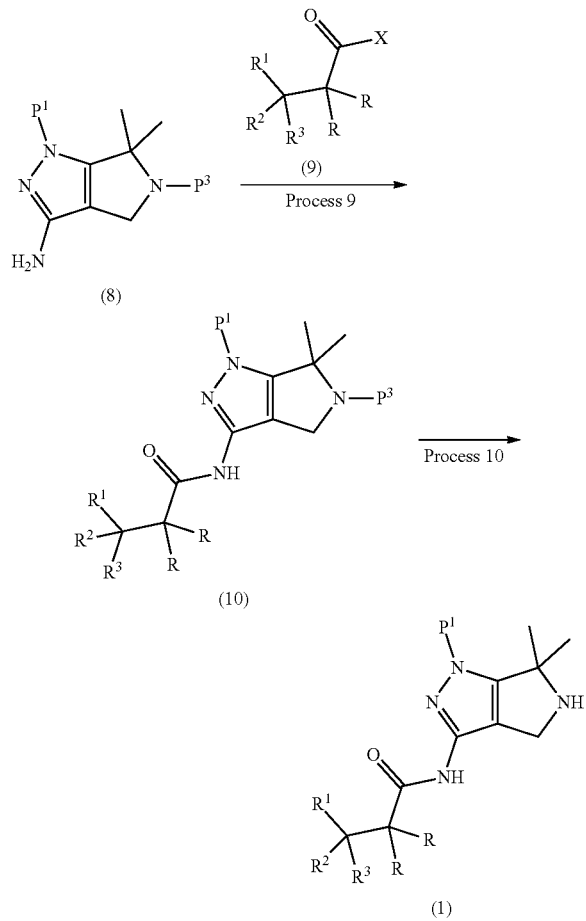

Compound (8) is a 3-amino-6,6-dimethyl-4,6-dihydropyrrolo [3,4-c]pyrazole, wherein a nitrogen atom on the pyrazole skeleton may be substituted with a $P^1$ group and the nitrogen atom at position 5 may be substituted with a $P^3$ group. Note that the $P^1$ group should be able to replace the acidic proton of the pyrazole in the 4,6-dihydropyrrolo [3,4-c]pyrazole skeleton. Consequently, the $P^1$ group may be substituted at the 1-position or at the 2-position of the 4,6-dihydropyrrolo [3,4-c]pyrazole skeleton. For convenience, the explanation will use chemical formulas with the substitution at position 1 of the 4,6-dihydropyrrolo [3,4-c] pyrazole skeleton for compound (8) and compound (10).

In compound (8), $P^1$ is identical to that which is defined in the method for producing the compound (I). The $P^3$ group can be any substituent group known to those skilled in the art as a protective group for amino groups. The $P^3$ group may be, for example: a $C_{7-11}$ aralkyl group (which may be substituted), such as a benzyl group, a p-methoxyphenylmethyl group, an o-nitrophenylmethyl group, or the like; a $C_{1-6}$ alkyl carbonyl group (which may be substituted), such as an acetyl group, a trifluoroacetyl group, or the like; a $C_{6-10}$ arylcarbonyl group (which may be substituted), such as a benzoyl group, or the like; a $C_{1-6}$ alkoxycarbonyl group (which may be substituted), such as a methoxycarbonyl group, an ethoxycarbonyl group, a Boc group (tert-butoxycarbonyl group), a Cbz group (benzyloxycarbonyl group), an Fmoc group (fluorenylmethyloxycarbonyl group), a Teoc group (trimethylsilylethyl oxycarbonyl group), or the like; an alkenyloxycarbonyl group, such as an Alloc group (allyloxycarbonyl group), or the like; an alkylsulfonyl group, such as a methanesulfonyl group, or the like; or a $C_{6-10}$ arylsulfonyl group (which may be substituted), such as a p-toluenesulfonyl group, or the like.

In compounds (9) and (10), R, $R^1$, $R^2$, and $R^3$ are identical to that which is defined for compound (I). The X group can be any substituent group known to those skilled in the art as an extraction group for amino groups. X may be, for example: a halogen atom; an imidazolyl group; an aminooxy group such as a succinyl-N-oxy group, a benzotriazolyl-N-oxy group, or the like; or an acyloxy group such as a pivaloyloxy group, a benzoyloxy group, or the like. X may be a hydroxyl group instead.

If compound (9) is a carboxylic acid (that is, if X is a hydroxyl group), it may be converted to an acid anhydride through a method known to those skilled in the art and then reacted with compound (8), and a reagent known to those skilled in the art as a condensation agent for amide bond forming reactions may be used to react with compound (8).

(Process 9) Process 9 is a process for reacting compound (8) with compound (9) to produce a compound (10).

The amount of the compound (9) used is preferably 1 to 10 moles, and more preferably 1 to 3 moles, per 1 mole of compound (8).

In Process 9, the reaction may be carried out in a solvent or without a solvent. There is no particular limitation on the solvent, insofar as it does not have an effect on the reaction, and preferably it is an organic solvent. The organic solvent may be, for example, dichloromethane, diethyl ether, tetrahydrofuran (THF), N,N-dimethylformamide (DMF), or dimethyl sulfoxide (DMSO).

In Process 9, a base may further be added to accelerate the reaction. The base may be an organic amine such as, for example, triethylamine (TEA), diisopropylethylamine (DIPEA), 1,5-diazabicyclo [4.3.0]nonene (DBN), 1,8-diazabicyclo [5.4.0]undecene (DBU), pyridine, 4-dimethylaminopyridine (DMAP), or the like.

The amount of the base added is preferably 1 to 20 moles, and more preferably 1 to 5 moles, per 1 mole of compound (8).

The reaction temperature in Process 9 can be set as appropriate by a person skilled in the art. Usually the reaction temperature is between −40 and 100° C., and preferably between −20 and 20° C.

(Process 10) Process 10 is a process for carrying out a deprotection reaction on compound (10) to produce compound (1). The $P^3$ group removal reaction may be carried out by a method that is known to those who are skilled in the art (such as a method described in Protective Groups in Organic Synthesis, Fourth Edition, by T. W. Greene and P. G. M. Wuts, John Wiley & Sons Inc. (2006), or the like).

<Production Method for Compound (8)>

Compound (8) may be produced, for example, through the method below, using compound (11) as a starting material. In general formulas (13), (14) and (15), $P^3$ is identical to that which is defined in compound (8).

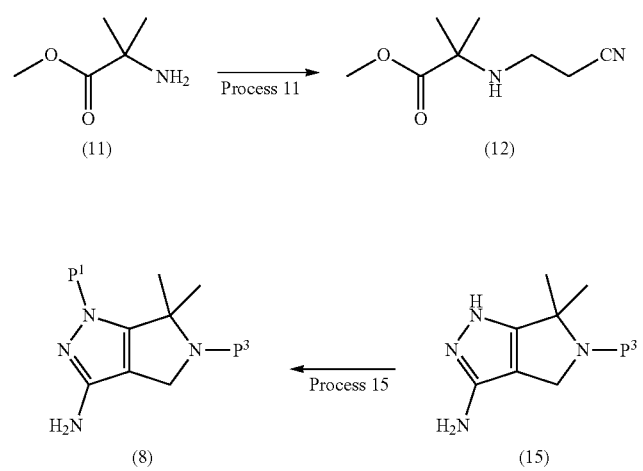

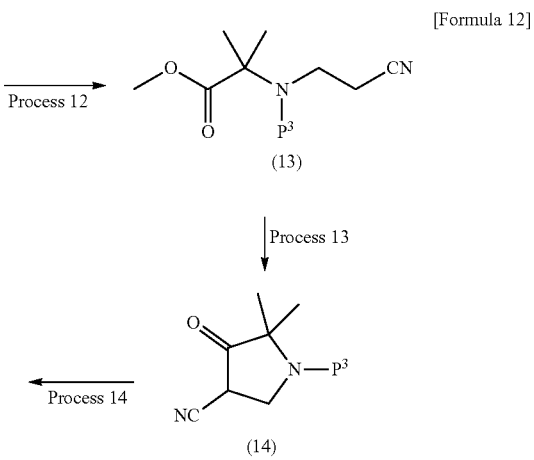

[Formula 12]

(Process 11) Process 11 is a process for reacting compound (11) with acrylonitrile to produce compound (12).

The amount of the acrylonitrile used is preferably 1 to 10 moles, and more preferably 1 to 3 moles, per 1 mole of compound (11).

In Process 11, the reaction may be carried out in a solvent or without a solvent. There is no particular limitation on the solvent, insofar as it does not have an effect on the reaction, and preferably it is an aqueous solvent.

In Process 11, a base may further be added to accelerate the reaction. The base may be an inorganic base such as potassium hydroxide, or the like. The amount of base added is preferably between 0.8 and 2 moles per 1 mole of compound (11).

The reaction temperature in Process 11 can be set as appropriate by a person skilled in the art. Usually the reaction temperature is between 0 and 100° C., and preferably between 5° and 90° C.

(Process 12) Process 12 is a process for protecting the amino group of compound (12) with the $P^3$ group, to produce compound (13). The protection reaction for the amino group by the $P^3$ group may be carried out by a method that is known to those who are skilled in the art and, for example, may be carried out following a method described in Protective Groups in Organic Synthesis, Fourth Edition, by T. W. Greene and P. G. M. Wuts, John Wiley & Sons Inc. (2006), or the like.

(Process 13) Process 13 is a process for carrying out a cyclization reaction on compound (13) to produce compound (14). In Process 13, the reaction may be carried out in a solvent or without a solvent. There is no particular limitation on the solvent, insofar as it does not have an effect on the reaction, and preferably it is an organic solvent. The organic solvent may be, for example, diethyl ether, tetrahydrofuran (THF), 1,4-dioxane, N,N-dimethylformamide (DMF), toluene, or the like.

In Process 13, a base may further be added to accelerate the reaction. The base may be, for example, sodium hydride, potassium hydride, sodium methoxide, sodium ethoxide, n-butyl lithium, potassium tert-butoxide, or the like. The amount of base added is preferably between 1 and 3 moles per 1 mole of compound (13).

The reaction temperature in Process 13 can be set as appropriate by a person skilled in the art. Usually the reaction temperature is between 2° and 150° C., and preferably between 5° and 100° C.

(Process 14) Process 14 is a process for reacting compound (14) with hydrazine to produce compound (15).

In Process 14, the reaction may be carried out in a solvent or without a solvent. There is no particular limitation on the solvent, insofar as it does not have an effect on the reaction, and preferably it is an organic solvent. The organic solvent may be, for example, ethanol, n-propanol, n-butanol, or the like.

In Process 14, an acid may further be added to accelerate the reaction. The acid may be, for example, acetic acid, hydrochloric acid, sulfuric acid, or the like. The amount of acid added is preferably between 1 and 10 moles per 1 mole of compound (14).

The reaction temperature in Process 14 can be set as appropriate by a person skilled in the art. Usually the reaction temperature is between 2° and 150° C., and preferably between 5° and 150° C.

(Process 15) Process 15 is a process for protecting the amino group of compound (15) with the $P^1$ group, to produce compound (8). The protection reaction for the amino group by the $P^1$ group may be carried out by a method that is known to those who are skilled in the art and, for example, may be carried out following a method described in Protective Groups in Organic Synthesis, Fourth Edition, by T. W. Greene and P. G. M. Wuts, John Wiley & Sons Inc. (2006), or the like.

Another embodiment according to the present invention is a method for treating or preventing cancer, an inflammatory disease, an allergic disease, or a chronic respiratory disease, including administration of a compound represented by general formula (I), or a pharmacologically acceptable salt thereof, to a subject in need thereof. Here the "subject in need of a compound represented by the general formula (I) or a pharmacologically acceptable salt thereof" is, for example, a patient suffering from cancer, an inflammatory disease, an allergic disease, or a chronic respiratory disease.

Examples of the aforementioned cancers include, for example, multiple myeloma, chronic myelogenous leukemia, hematologic tumors, hematological malignant diseases, pediatric leukemia, pediatric lymphoma, hodgkin's disease, lymphocytic lymphoma, cutaneous lymphoma, acute leukemia, chronic leukemia, acute lymphoblastic leukemia, acute myelocytic leukemia, chronic myelocytic leukemia, plasmacytoid neoplasm, lymphocyte-like neoplasm, AIDS-related and other hematologic cancers; bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer (including squamous cell carcinoma), fibrosarcoma, rhabdomyosarcoma, astrocytoma, neuroblastoma, glioma and schwannoma, melanoma, epithelioma, teratocarcinoma, osteosarcoma, xeroderma pigmentosum, keratinocytoma, follicular carcinoma of the thyroid, Kaposi's sarcoma, and other solid tumors. Cancers for which the compounds of the present invention are particularly effective include, for example, bladder cancer, breast cancer, colon cancer, kidney cancer, liver cancer, lung cancer, esophageal cancer, gallbladder cancer, ovarian cancer, pancreatic cancer, stomach cancer, cervical cancer, thyroid cancer, head and neck cancer, prostate cancer, cutaneous cancer, tumors of mesenchymal origin, tumors of the central or peripheral nervous system, hematopoietic tumors of the lymphatic system, hematopoietic tumors of the myeloid system, teratomas, osteosarcomas, and Kaposi's sarcomas.

The inflammatory diseases referenced above include autoimmune diseases and, more specifically, include rheumatoid arthritis, psoriasis, multiple sclerosis, and inflammatory bowel disease.

The chronic respiratory diseases referenced above include, for example, chronic obstructive pulmonary disease (COPD).

The allergic diseases referenced above include, for example, atopic dermatitis.

When administering the compound represented by general formula (I) or the pharmacologically acceptable salt thereof, it may be administered in combination with other drugs. More specifically, a pharmaceutical composition containing a compound represented by general formula (I) or the pharmacologically acceptable salt thereof and another composition containing the other drug can be prepared separately and administered simultaneously or at different times. Moreover, the pharmaceutical composition that includes the compound represented by the general formula (I) or the pharmacologically acceptable salt thereof may further include the other drug.

"The other drug" means drug that is needed by the subject, such as, for example, an anti-cancer drug, an anti-rheumatic drug, a psoriasis drug, a multiple sclerosis drug, an inflammatory bowel disease drug, a chronic obstructive pulmonary disease drug, an atopic dermatitis drug, or the like.

The "other drug" may be, for example, a tyrosine kinase inhibiting agent (for example, Gefitinib, Erlotinib, Dasatinib, Bosutinib, Vandetanib, Sunitinib, Axitinib, Pazopanib, Lenvatinib, Lapatinib, sorafenib, Afatinib, Imatinib, Nilotinib, Nintedanib, Crizotinib, Seritinib, Alecitinib, Ibrutinib, Vemphenib, Taburafenib, or Trametinib), an immunostimulant, a DNA alkylating agent (for example, Cyclophosphamide, or Ifosfamide), a DNA synthesis inhibiting agent, a platinum preparation (for example, Cisplatin, Oxaliplatin, or Carboplatin), an anti-metabolic agent, A topoisomerase I inhibiting agent, a topoisomerase II inhibiting agent, a tubulin agonist, a microtubule inhibiting agent (for example, Vinblastine, Vincristine, Vindesine, or Colchicine), a hormone antagonist, an aromatase inhibiting agent, a differentiation inducing agent, a proteosome inhibiting agent, a phospholipid kinase inhibiting agent, an adenosine deaminase inhibiting agent, an angiogenesis inhibiting agent, a histone deacetylase (HDAC) inhibiting agent, a BET bromodomain inhibiting agent, a histone demethylase inhibiting agent, a histone methyltransferase inhibiting agent, a matrix metalloproteinase inhibiting agent, a farnesyltransferase inhibiting agent, a bisphosphonate, an Hsp90 inhibiting agent, a kinesin Eg5 inhibiting agent, a serine threonine kinase inhibiting agent, an anti-cytokine agent, an immunosuppressant (for example, D-penicillamine), an active vitamin D3 preparation (for example, 5,6-trans-cholecalciferol, 2,5-hydroxycholecalciferol, 1-alpha-hydroxycholecalciferol, or calcipotriol), a vitamin D2 derivative (for example, 5,6-trans-ergocalciferol), an S1P1 receptor antagonist (for example, Fingolimod, Iguratimod), an interferon preparation (for example, interferon alpha, interferon alfa-2b, interferon β1a, or interferon β1b), an anticholinergic, a leukotriene antagonist, a PDE4 inhibiting agent (for example, Roflumilast, Apremilast, or Tetomilast), a prostaglandin (PG) D2 receptor antagonist, a neutrophil elastase inhibiting agent, an antihistamine (for example, sodium cromoglycate), a nonsteroidal anti-inflammatory drug (for example, aspirin, a salicylic acid derivative (for example, salicylic acid, sodium salicylate, or methyl salicylate), acetaminophen, indomethacin, ibuprofen, ketoprofen, sulpirine, antipyrine, loxoprofen, ethenzamide, alkofenac, aceclofenac, sulindac, or the like), a cyclooxygenase inhibiting agent (including a COX-1 selective inhibiting agent or a COX-2 selective inhibiting agent) (for example, Etodolac, Meloxicam, Nabumetone, Zaltoprofen, Lornoxicam, Celecoxib, Etoricoxib, or Valdecoxib), a free nitric oxide nonsteroidal anti-inflammatory drug, a gold preparation (for example, sodium gold thiomaltate, or Auranofin), an aminosalicylic acid preparation, an antimalarial agent, a pyrimidine synthesis inhibiting agent, a TNF inhibiting agent, an interleukin inhibiting agent, an interleukin receptor antagonist, an interleukin receptor agonist, a B-cell activation inhibiting agent, a co-stimulatory molecule-related protein preparation, a gene modulating agent, a cytokine production inhibiting agent, a TNF-alpha converting enzyme inhibiting agent, an IL-1beta converting enzyme inhibiting agent, a chemokine antagonist, a therapeutic vaccine, a gene therapy drug, an antisense compound, a proteasome inhibiting agent, a JAK inhibiting agent, a selectin inhibiting agent, an ELAM-1 inhibiting agent, a VCAM-1 inhibiting agent, an ICAM-1 inhibiting agent, a Tyk2 inhibiting agent (for example, a compound described in WO2010/142752 or a salt thereof), a T cell inhibiting agent, an inosine monophosphate dehydrogenase (IMPDH) inhibiting agent, an adhesion inhibiting agent, thalidomide, a cathepsin inhibiting agent (for example, a cathepsin B inhibiting agent), a glucose-6-phosphate dehydrogenase inhibiting agent, a dihydroorotate dehydrogenase (DHODH) inhibiting agent, a phospholipase A2 inhibiting agent, an Inos inhibiting agent, a microtubule stimulants, a Mhc class II antagonist, a CD4 antagonist, a CD23 antagonist, a leukotriene B4 receptor antagonist, a 5-lipoxygenase inhibiting agent, an osteogenesis stimulating agent, a dipeptidyl peptidase inhibiting agent, a collagenolytic agent, a capsaicin cream, a sulfa drug, a hyaluronic acid derivative (for example, sodium hyaluronate), glucosamine sulfate, a CD20 inhibiting agent, a CD52 inhibiting agent, an anti-allergic drug (for example, an anti-asthma drug, an atopic dermatitis medication, or an allergic rhinitis medication), an opioid receptor agonist (for example, a morphine or a salt thereof (for example, morphine hydrochloride), Pethidine, Levorphanol, or Oxymorphone), an immunoglobulin, glatiramer acetate, a T-cell receptor vaccine, an adhesion molecule inhibiting agent, a muscle relaxant, a local anesthetic (for example, Lidocaine), Ketamine, a muscarinic receptor (M1 receptor, M2 receptor, or M3 receptor) antagonist (for example, iprotropium bromide, oxytropium bromide, or flutropium bromide), a β receptor (including β1 receptor, β2 receptor, β3 receptor, and β4 receptor) agonist (for example, isoprenaline hydrochloride, salbutamol sulfate, prokaterol hydrochloride, terbutaline sulfate, trimethoquinol hydrochloride, turobuterol hydrochloride, orciprenaline sulfate, phenoterol hydrobromide, ephedrine hydrochloride), a combination beta-receptor agonist and inhaled steroid, a vitamin derivative, an adrenal corticosteroid, an anti-IL-6 antibody (for example, Tocilizumab), a MAPK inhibiting agent (for example, SCI0469, BIRB796, SB203580, VX-702, Pamapimod, PH797804, Vemurafenib, Dabrafenib, Trametinib, Cobimetinib, CC-359, CC-930, Bentamapimod, or XG-104), an IL-8 antagonist, a CXCR1-CXCR2 dual antagonist (for example, Reparixin), a CCR9 antagonist (for example, bersilnon sodium), or the like.

An immunostimulant is an agent that inhibits an immune checkpoint selected from the group consisting of (1) CTLA-4, PD-1, PD-L1, TIM-3, KIR, LAG-3, VISTA, and BTLA, or (2) an agent that activates an immune checkpoint selected from the group consisting of OX40 (a.k.a. CD134), IL-10R, GITR, CD27, CD28, CD137, and ICOS (a.k.a. CD278). Drugs that inhibit immune checkpoints include Nivolumab, Pembrolizumab, Ipilimumab, Atezolizumab, Avelumab, Durvalumab, Tremelimumab, Pidilizumab, JNJ-63723283, BMS-936559, LY3300054, FAZ053, and MPDL3280A. Drugs that activate immune checkpoint proteins include AM0010 (a.k.a. Pegilodecakin), GSK3174998, MOXR0916 (a.k.a. Tavolimab), PF-04518600, MEDI0562, TRX518, MEDI1873, Valrirumab, Urelumab, Utomilumab, and MEDI-570.

The "other drug" may be, for example, Doxorubicin, Taxotere, Taxol, Etoposide, Irinotecan, Topotecan, Paclitaxel, Docetaxel, Epothilone, Tamoxifen, 5-fluorouracil, Methotrexate, Temozolomide, SCH 66336, R115777, L778,123, BMS 214662, Panitumumab, Palbociclib, Cytarabine (aka ara-C), Adriamycin, Cytoxan, Gemcitabine, Uracil mustard, Chlormethine, Melphalan, Chlorambucil, Pipobroman, triethylene melamine, triethylene thiophosphoramine, Ofatumumab, Busulfan, Carmustine, Lomustine, Streptozocin, Dacarbazine, Phloxuridine, 6-mercaptopurine, 6-thioguanine, Regorafenib, Ramucirumab, Fludarabine phosphate, Holinate, Pentostatin, Bleomycin, Dactinomycin, Daunorubicin, Doxorubicin, Epirubicin, Idarubicin, Mithramycin, Deoxycholomycin, Mytomycin-C, L-asparaginase, Teniposide, 17α-ethinylestradiol, Diethylstilbestrol, testosterone, prednisone, Fluoxymesterone, Dromostanolone propionate, Teslactone, megestrol acetate, methyl prednisolone, methyl testosterone, Prednisolone, Chlorotrianisene, hydroxy progesterone, Aminoglutethimide, Estramustine, Medroxyprogesterone acetate, Leuprolide acetate, Flutamide, Toremifene, Goserelin, Hydroxyurea, Amsacrine, Procarbazine, Mitotene, Mitoxantrone, Levamisole, Navelben, Anastrazole, Letrasol, Capecitabine, Reloxafin, Doloroxafine, Hexamethylmelamine, Bevacizumab, Omalizumab, Mepolizumab, Gemtuzumab Ozogamicin, Mogamulizumab, Pertuzumab, Ocrelizumab, Alemtuzumab, Inotuzumab, Tositumomab, Bortezomib, Ibritumomab Tiuxetan, arsenic trioxide, Vinorelbine, Porfimer, Thiotepa, Arthrotamine, Trastuzumab, Letrozole, Fulvestrant, Exemestane, Rituximab, Cetuximab, Basiliximab, Tolmetin, Phenoprofen, Thiaprofenate, Meclofenamate, Teoxicam, Phenacetin, Miglenine, Mefenamic acid, Flufenamic acid, Phenylbutazone, naproxen, Oxaprozin, Flurbiprofen, Fembufen, Planoprofen, Fluctafenine, Piroxicam, Epirizole, Thiaramide hydrochloride, Gabexate mesylate, Camostat mesylate, Urinastatin, Probenecid, Sulfinpyrazone, Benzbromarone, Allopurinol, Brentuximab Vedotin, Atropine, Scopolamine, Sulfasalazine, Mesalazine, Olsalazine, Balsalazide, Chloroquine, Leflunomide, Tacrolimus, Infliximab, Etanercept, Adalimumab, Certolizumab Pegol, golimumab, PASSTNF α, a soluble TNF-alpha receptor, a TNF-alpha binding protein, an anti-TNFα antibody, Denosumab, Anakinra, a soluble IL-1 receptor antibody (for example, rilonacept, or canakinumab), tocilizumab, IL-10, Ustekinumab, Briakinumab, Secukinumab (AIN-457), Ixekizumab (LY-2439821), AMG827, Rituxan, Belimumab, Abatacept, BMS-582949, an inhibitor for a molecule involved in signal transduction (for example, NF-κ, NF-κB, IKK-1, IKK-2, or AP-1) (for example, dimethyl fumarate, dehydroxymethyl epoxyquinomycin, DTCM-glutarimide, sesquiterpene lactone, Resveratrol, Curcumin, Diindolylmethane noscapine, Parthenolide, Ixazomib, Carfilzomib, Delanzomib, Marizomib, MLN-4924, EVID-2560, EVID-0354, IMD-1041, BAY-11-7082, BAY-11-7085, MLN120B, BMS-345541, SC-514, PS-1145, Denosumab, Vorinostat, Romidepsin, SN-50, or T-5224), urea, Vernacasan, HMPL-004, Denileukin diftitox, CCX025, N-{4-chloro-2-[(1-oxydopyridin-4-yl)carbonyl]phenyl}-4-(propan-2-yloxy) benzenesulfonamide, an MCP-1 antagonist, Irbesartan, a TNF-alpha vaccine, ISIS-104838, Natalizumab, Vedolizumab, AJM300, TRK-170, E6007, MX-68, BMS-188667, CKD-461, Limequoron, Cyclosporine A, Mizoribine, Gusperimus, Sirolimus, Temsirolimus, Everolimus, an anti-lymph serum, a dried sulfated immunoglobulin, erythropoietin, a colony-stimulating factor, atiprimod dihydrochloride, Azathioprine, Tofacitinib, Baricitinib, Carfilzomib, Ruxolitinib, dexamethasone, Hexestrol, methimazole, Betamethasone, Triamcinolone acetonide, Fluocinonide, Fluocinolone acetonide, cortisone acetate, hydrocortisone, Fluorometholone, Beclomethasone propionate, Estriol, Mycophenolate Mofetil, Aricafolcene sodium, V-85546, VAS203, Rheumacon, Zanolimumab, DW-1350, Zyrton, Synvisc (hylan G-F 20), Orthovisc, Atacicept, Brisibimod, Tizanidine, Eperisone, Afroqualone, Baclofen, diazepam, Dantrolene sodium, Theophylline, Aminophylline, Tranilast, Lepirinast, Anlexanone, Ibudilast, Ketotifen, Terfenadine, Mequitazine, Azelastine, Ozagrel hydrochloride, Pranlukast hydrate, Serratrodust, Ciclesonide, Chlorpheniramine maleate, Alimemazine tartrate, Clemastine fumarate, Homochlorocyclidine hydrochloride, Fexofenadine, Ketotifen fumarate, Cetirizine hydrochloride, Oxatomide, Evastin, Epinastine hydrochloride, Loratadine, Tramadol, Promethazine, Hydroxyzine, Homochlorcyclidine, Cyproheptadine, Mektadine, Emedestine fumarate, Pseudoephedrine, Bepotastine Besilate, Levocetirizine, Olopatadine hydrochloride, Mofetil mycophenolate, Daclizumab, Galiximab, Metformin hydrochloride, Vizirizumab, Aminopterin, Fezakinumab, Ruxolitinib phosphate, ixekizumab, Guselkumab, SLx-2119, PRX-167700, Thiotropium bromide, Salmeterol xinafoate, Formoterol fumarate, Fluticasone propionate, Beclomethasone propionate, Budesonide, a combination drug of Salmeterol xinafoate and Fluticasone propionate, or the like.

Preferred "other drugs" are 5-fluorouracil, oxaliplatin, and irinotecan.

EXAMPLES OF EMBODIMENT

While in the below the present invention is explained in greater detail through embodiments (Embodiments 1 to 11), reference examples (Reference Examples 1 and 2), and test examples (Test Examples 1 to 8) of compounds and pharmaceutically acceptable salts of the present embodiments, these examples are to aid in understanding the present invention, and do not limit the scope of the present invention.

An EPCLC-W-Prep 2XY A-Type (product name, manufactured by YAMAZEN Corp.) was used for purification through preparative column chromatography.

The stationary phase used in the purification by preparative column chromatography is as follows.

Silica gel: UNIVERSAL (trade name) COLUMN Silica Gel 40 m 60 Å

DIOL silica gel: CHROMATOREX (trade name) DIOL MB 100-40/75 (manufactured by Fujisilicia Chemical Co., Ltd.)

If more than one mass spectrum value was observed due to the presence of isotopes, only the one with the smallest m/z is listed.

Unless otherwise stated, $^1$H-NMR is expressed as chemical shifts (δ) with tetramethylsilane as the internal standard (0 ppm), and coupling constants (J values) are expressed in Hz. The abbreviations for the splitting patterns of each peak have the following meanings: s: singlet, d: doublet, t: triplet, q: quartet, br s: broad singlet, m: multiplet.

The abbreviations used in the examples and reference examples are used with the meanings with which they are generally used in the fields of organic chemistry and pharmaceutical sciences. Specifically, each abbreviation is understood by those skilled in the art as follows:

ATP: Adenosine triphosphate
CI: Chemical Ionization
DIPEA: N,N-diisopropylethylamine
DMF: N,N-dimethylformamide
DMSO: Dimethylsulfoxide
DPPA: Diphenylphosphonyl azide
DTT: Dithiothreitol
DUIS: Dual ion source
FBS: Fetal Bovine Serum
HEPES: N-2-hydroxyethylpiperazine-N'-2-ethanesulfonic acid
MBP: Myelin basic protein
MOPS: 3-morpholinopropanesulfonic acid
n-: Normal
TCA: Trichloroacetic acid
TEA: Triethylamine
TFA: Trifluoroacetic acid
tert-: Tertiary
THF: Tetrahydrofuran
TLC: Thin layer chromatography Embodiment 1

3-(1-(tert-butyl) cyclobutane-1-carboxamide)-N-(2-fluorophenyl)-6,6-dimethyl-4,6-dihydropyrrolo [3,4-c]pyrazole-5 (1H)-carboxamide To a dehydrated dichloromethane solution (1.0 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.1 mg) that was synthesized in the same manner as in Reference Example 2, 2-fluorophenyl isocyanate (21.8 mg, 0.018 mL) was added dropwise at 0° C. under an argon atmosphere, after which the reaction was carried out at 0° C. for 4 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2-fluorophenyl) carbamoyl)-6,6-dimethyl-5,6-dihydropyrrolo [3,4-c]pyrazole-2 (4H)-carboxylate (54.3 mg) as a light yellow solid.

To a THF solution (1.0 mL) of the ethyl 3-(1-(tert-butyl) cyclobutane-1-carboxamide)-5-((2-fluorophenyl) carbamoyl)-6,6-dimethyl-5,6-dihydropyrrolo [3,4-c]pyrazole-2 (4H)-carboxylate (54.3 mg) that was produced, N,N-dimethyl ethylenediamine (0.063 mL) was added at room temperature under an argon atmosphere, after which the reaction was carried out at room temperature for 2.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50), and the fraction containing the target product was concentrated under reduced pressure and dried under reduced pressure. The concentrated residue produced was dissolved in an acetonitrile/water mixed solvent and lyophilized to produce the indicated compound (38.9 mg, 78% yield) as a white solid.

Mass spectrum (ESI, m/z):428[M+H]$^+$ $^1$H-NMR spectrum (400 MHz, DMSO-d$_6$) δ: 12.55-11.69 (m, 1H), 9.85 (br s, 1H), 7.85 (br s, 1H), 7.56 (br s, 1H), 7.22-7.04 (m, 3H), 4.75-4.55 (m, 2H), 2.37-2.27 (m, 2H), 2.22-2.08 (m, 2H), 1.66 (s, 8H), 1.02-0.90 (m, 9H)

Embodiment 2

3-(1-(tert-butyl) cyclobutane-1-carboxamide)-N-(o-tolyl)-6,6-dimethyl-4,6-dihydropyrrolo [3,4-c]pyrazole-5 (1H)-carboxamide To a dehydrated dichloromethane solution (1.0 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.7 mg) that was synthesized in the same manner as in Reference Example 2, o-tolyl isocyanate (21.4 mg, 0.020 mL) was added dropwise at 0° C. under an argon atmosphere, after which the reaction was carried out at 0° C. for 3 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-6,6-dimethyl-5-(o-tolyl carbamoyl)-5,6-dimethyl-5,6-dihydropyrrolo [3,4-c]pyrazole-2 (4H)-carboxylate (60 mg) as a colorless oily substance.

To a THF solution (1.0 mL) of the ethyl 3-(1-(tert-butyl) cyclobutane-1-carboxamide)-6,6-dimethyl-5-(o-tolyl carbamoyl)-5,6-dihydropyrrolo [3,4-c]pyrazole-2 (4H)-carboxylate (60 mg) that was produced, N,N-dimethyl ethylenediamine (0.064 mL) was added at room temperature under an argon atmosphere, after which the reaction was carried out at room temperature for 14.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (38.3 mg, 77% yield) as a white solid.

Mass spectrum (ESI, m/z):424[M+H]$^+$ $^1$H-NMR spectrum (400 MHz, DMSO-d$_6$) δ: 12.45-11.84 (m, 1H), 10.08-9.66 (m, 1H), 7.88-7.52 (m, 1H), 7.32-7.19 (m, 1H), 7.16 (d, J=7.5 Hz, 1H), 7.14-7.06 (m, 1H), 7.06-6.98 (m, 1H), 4.65 (br s, 2H), 2.38-2.26 (m, 2H), 2.23-2.07 (m, 5H), 1.66 (br s, 8H), 0.95 (s, 9H)

Embodiment 3

3-(1-(tert-butyl) cyclobutane-1-carboxamide)-N-(2-chloro-6-methylphenyl)-6,6-dimethyl-4,6-dihydropyrrolo [3,4-c]pyrazole-5 (1H)-carboxamide To a dehydrated dichloromethane solution (1.0 mL) of ethyl 3-(1-(tert-butyl) cyclobutane-1-carboxamide)-6,6-dimethyl-5,6-dihydropyrrolo [3,4-c]pyrazole-2 (4H)-carboxylate (43.2 mg, 0.114 mmol) that was synthesized in the same manner as in Reference Example 2, 2-chloro-6-methylphenyl isocyanate (28.3 mg, 0.023 mL) was added dropwise at 0° C. under an argon atmosphere, after which the reaction was carried out at 0° C. for 4 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (silica gel, n-hexane: ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2-chloro-6-methylphenyl) carbamoyl)-6,6-dimethyl-5,6-dihydropyrrolo [3,4-c]pyrazole-2 (4H)-carboxylate (54.5 mg) as a white foamy substance.

To a THF solution (1.0 mL) of the ethyl 3-(1-(tert-butyl) cyclobutane-1-carboxamide)-5-((2-chloro-6-methylphenyl) carbamoyl)-6,6-dimethyl-5,6-dihydropyrrolo [3,4-c]pyrazole-2 (4H)-carboxylate (54.5 mg) that was produced, N,N-dimethyl ethylenediamine (0.062 mL) was added at room temperature under an argon atmosphere, after which the reaction was carried out at room temperature for 14.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (40.4 mg, 78% yield) as a white solid.

Mass spectrum (ESI, m/z):458[M+H]$^+$ $^1$H-NMR spectrum (400 MHz, DMSO-d$_6$) δ:12.47-11.81 (m, 1H), 10.09-9.65 (m, 1H), 8.03-7.57 (m, 1H), 7.30 (dd, J=1.3, 7.7 Hz, 1H), 7.22-7.17 (m, 1H), 7.17-7.11 (m, 1H), 4.63 (br s, 2H), 2.37-2.26 (m, 2H), 2.22 (s, 4H), 1.64 (br s, 8H), 0.95 (s, 9H)

Embodiment 4

3-(1-(tert-butyl) cyclobutane-1-carboxamide)-N-(5-fluoro-2-methylphenyl)-6,6-dimethyl-4,6-dihydropyrrolo [3,4-c]pyrazole-5 (1H)-carboxamide To a dehydrated dichloromethane solution (1.0 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.0 mg) that was synthesized in the same manner as in Reference Example 2, 5-fluoro-2-methylphenyl isocyanate (24.7 mg, 0.021 mL) was added dropwise at 0° C. under an argon atmosphere, after which the reaction was carried out at 0° C. for 4 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (silica gel, n-hexane: ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((5-fluoro-2-methylphenyl) carbamoyl)-6,6-dimethyl-5,6-dihydropyrrolo [3,4-c]pyrazole-2 (4H)-carboxylate (59 mg) as a white foamy substance.

To a THF solution (1.0 mL) of the ethyl 3-(1-(tert-butyl) cyclobutane-1-carboxamide)-5-((5-fluoro-2-methylphenyl) carbamoyl)-6,6-dimethyl-5,6-dihydropyrrolo [3,4-c]pyrazole-2 (4H)-carboxylate (59 mg) that was produced, N,N-dimethyl ethylenediamine (0.063 mL) was added at room temperature under an argon atmosphere, after which the reaction was carried out at room temperature for 1.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50), and the fraction containing the target product was concentrated under reduced pressure and dried under reduced pressure. The concentrated residue produced was dissolved in an acetonitrile/water mixed solvent and lyophilized to produce the indicated compound (41.6 mg, 81% yield) as a white solid.

Mass spectrum (ESI, m/z):442[M+H]$^+$ $^1$H-NMR spectrum (400 MHz, DMSO-d$_6$) δ: 12.44-11.94 (m, 1H), 10.06-9.72 (m, 1H), 7.86-7.49 (m, 1H), 7.17 (dd, J=7.1, 8.0 Hz, 2H), 6.83 (dt, J=2.8, 8.5 Hz, 1H), 4.66 (br s, 2H), 2.36-2.24 (m, 2H), 2.23-2.08 (m, 5H), 1.66 (br s, 8H), 0.95 (s, 9H)

Embodiment 5

3-(1-(tert-butyl) cyclobutane-1-carboxamide)-N-(2,5-dimethylphenyl)-6,6-dimethyl-4,6-dihydropyrrolo [3,4-c]pyrazole-5 (1H)-carboxamide To a dehydrated dichloromethane solution (1.0 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.1 mg) that was synthesized in the same manner as in Reference Example 2, 2-isocyanate-1,4-dimethyl benzene (24.0 mg, 0.023 mL) was added dropwise at 0° C. under an argon atmosphere, after which the reaction was carried out at 0° C. for 3 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2,5-dimethylphenyl) carbamoyl)-6,6-dimethyl-5,6-dihydropyrrolo [3,4-c]pyrazole-2 (4H)-carboxylate (51.9 mg) as a white solid.

To a THF solution (1.0 mL) of the ethyl 3-(1-(tert-butyl) cyclobutane-1-carboxamide)-5-((2,5-dimethylphenyl) carbamoyl)-6,6-dimethyl-5,6-dihydropyrrolo [3,4-c]pyrazole-2 (4H)-carboxylate (50.5 mg [net: 48.8 mg]) that was produced, N,N-dimethyl ethylenediamine (0.063 mL) was added at room temperature under an argon atmosphere, after which the reaction was carried out at room temperature for 14.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (36.5 mg, 85% yield) as a white solid.

Mass spectrum (ESI, m/z):438[M+H]$^+$ $^1$H-NMR spectrum (400 MHz, DMSO-d$_6$) δ: 12.33 (br s, 1H), 9.79 (br s, 1H), 7.63 (br s, 1H), 7.11-7.01 (m, 2H), 6.84 (d, J=7.7 Hz, 1H), 4.62 (s, 2H), 2.36-2.26 (m, 2H), 2.24 (s, 3H), 2.13 (s, 5H), 1.65 (s, 8H), 0.95 (s, 9H)

Embodiment 6

3-(1-(tert-butyl) cyclobutane-1-carboxamide)-N-(2,6-dimethylchlorophenyl)-6,6-dimethyl-4,6-dihydropyrrolo [3,4-c]pyrazole-5 (1H)-carboxamide To a dehydrated toluene (1.0 mL) suspension of 2,6-dichlorobenzoic acid (43.2 mg), TEA (0.039 mL) and DPPA (62.6 mg, 0.049 mL) were added sequentially at room temperature under an argon atmosphere, and reacted while stirring for 0.5 hours at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (43.1 mg) that was synthesized in the same manner as in Reference Example 2, was added dropwise at 0° C., after which the reaction was carried out at 0° C. for 2 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2,6-dichlorophenyl) carbamoyl)-6,6-dimethyl-5,6-dihydropyrrolo [3,4-c]pyrazole-2 (4H)-carboxylate (65 mg) as a colorless oily substance.

To a THF solution (1.0 mL) of the ethyl 3-(1-(tert-butyl) cyclobutane-1-carboxamide)-5-((2,6-dichlorophenyl) carbamoyl)-6,6-dimethyl-5,6-dihydropyrrolo [3,4-c]pyrazole-2 (4H)-carboxylate (65 mg) that was produced, N,N-dimethyl ethylenediamine (0.062 mL) was added at room temperature under an argon atmosphere, after which the reaction was carried out at room temperature for 14 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (41.3 mg, 76% yield) as a white solid.

Mass spectrum (ESI, m/z):478[M+H]$^+$ $^1$H-NMR spectrum (400 MHz, DMSO-d$_6$) δ:12.46-11.87 (m, 1H), 10.03-9.75 (m, 1H), 8.25-8.03 (m, 1H), 7.49 (d, J=8.0 Hz, 2H), 7.32-7.24 (m, 1H), 4.73-4.51 (m, 2H), 2.37-2.26 (m, 2H), 2.25-2.08 (m, 2H), 1.77-1.55 (m, 8H), 1.03-0.86 (m, 9H)

Embodiment 7

3-(1-(tert-butyl) cyclobutane-1-carboxamide)-N-(2-chloro-6-fluorophenyl)-6,6-dimethyl-4,6-dihydropyrrolo [3,4-c]pyrazole-5 (1H)-carboxamide To a dehydrated toluene (1.0 mL) suspension of 2-chloro-6-fluorobenzoic acid (40.0 mg), TEA (29.0 mg, 0.040 mL) and DPPA (62.6 mg, 0.049 mL) were added sequentially at room temperature under an argon atmosphere, and reacted while stirring for 0.5 hours at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (43.3 mg) that was synthesized in the same manner as in Reference Example 2, was added dropwise at 0° C., after which the reaction was carried out at 0° C. for 2.5 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2-chloro-6-fluorophenyl) carbamoyl)-6,6-dimethyl-5,6-dihydropyrrolo [3,4-c]pyrazole-2 (4H)-carboxylate (55 mg) as a white foamy substance. To a THF solution (1.0 mL) of the ethyl 3-(1-(tert-butyl) cyclobutane-1-carboxamide)-5-((2-chloro-6-fluorophenyl) carbamoyl)-6,6-dimethyl-5,6-dihydropyrrolo [3,4-c]pyrazole-2 (4H)-carboxylate (55 mg) that was produced, N,N-dimethyl ethylenediamine (0.062 mL) was added at room temperature under an argon atmosphere, after which the reaction was carried out at room temperature for 14 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (37.2 mg, 71% yield) as a white solid.

Mass spectrum (ESI, m/z):462[M+H]$^+$
$^1$H-NMR spectrum (400 MHz, DMSO-$d_6$) δ:12.46-11.81 (m, 1H), 10.04-9.72 (m, 1H), 8.14-7.88 (m, 1H), 7.37-7.18 (m, 3H), 4.63 (br s, 2H), 2.38-2.26 (m, 2H), 2.22-2.07 (m, 2H), 1.64 (br s, 8H), 0.95 (s, 9H)

Embodiment 8

N-(2-bromo-6-methylphenyl)-3-(1-(tert-butyl) cyclobutane-1-carboxamide)-6,6-dimethyl-4,6-dihydropyrrolo [3,4-c]pyrazole-5 (1H)-carboxamide To a dehydrated toluene (1.0 mL) suspension of 2-bromo-6-methylbenzoic acid (50.7 mg), TEA (0.040 mL) and DPPA (63.9 mg, 0.050 mL) were added sequentially at room temperature under an argon atmosphere, and reacted while stirring for 0.5 hours at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.0 mg) that was synthesized in the same manner as in Reference Example 2, was added dropwise at 0° C., after which the reaction was carried out at 0° C. for 2 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 5-((2-bromo-6-methylphenyl) carbamoyl)-3-(1-(tert-butyl) cyclobutane-1-carboxamide)-6,6-dimethyl-5,6-dihydropyrrolo [3,4-c]pyrazole-2 (4H)-carboxylate (60 mg) as a white foamy substance.

To a THF solution (1.0 mL) of the ethyl 5-((2-bromo-6-methylphenyl)carbamoyl)-3-(1-(tert-butyl) cyclobutane-1-carboxamide)-6,6-dimethyl-5,6-dihydropyrrolo [3,4-c]pyrazole-2 (4H)-carboxylate (60 mg) that was produced, N,N-dimethyl ethylenediamine (0.066 mL) was added at room temperature under an argon atmosphere, after which the reaction was carried out at room temperature for 15 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50), and the fraction containing the target product was concentrated under reduced pressure and dried under reduced pressure. The concentrated residue produced was dissolved in an acetonitrile/water mixed solvent and lyophilized to produce the indicated compound (44.9 mg, 77% yield) as a white solid.

Mass spectrum (ESI, m/z):502[M+H]$^+$
$^1$H-NMR spectrum (400 MHz, DMSO-$d_6$) δ: 12.35 (br s, 1H), 9.96-9.68 (m, 1H), 7.85 (br s, 1H), 7.49-7.43 (m, 1H), 7.25-7.20 (m, 1H), 7.10-7.04 (m, 1H), 4.63 (s, 2H), 2.37-2.27 (m, 2H), 2.23 (s, 3H), 2.20-2.09 (m, 2H), 1.64 (s, 8H), 0.95 (s, 9H)

Embodiment 9

3-(1-(tert-butyl) cyclobutane-1-carboxamide)-N-(2-fluoro-3,6-dimethylphenyl)-6,6-dimethyl-4,6-dihydropyrrolo [3,4-c]pyrazole-5 (1H)-carboxamide To a dehydrated toluene (1.0 mL) suspension of 2-fluoro-3,6-dimethylbenzoic acid (39.1 mg) that was synthesized referencing the description in Reference Example 20 of WO2016/204153, TEA (0.040 mL) and DPPA (63.9 mg, 0.050 mL) were added sequentially at room temperature under an argon atmosphere, and reacted while stirring for 0.5 hours at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.1 mg) that was synthesized in the same manner as in Reference Example 2, was added dropwise at 0° C., after which the reaction was carried out at 0° C. for 2 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2-fluoro-3,6-dimethylphenyl) carbamoyl)-6,6-dimethyl-5,6-dihydropyrrolo [3,4-c]pyrazole-2 (4H)-carboxylate (64 mg) as a colorless oily substance. To a THF solution (1.0 mL) of the ethyl 3-(1-(tert-butyl) cyclobutane-1-carboxamide)-5-((2-fluoro-3,6-dimethylphenyl) carbamoyl)-6,6-dimethyl-5,6-dihydropyrrolo [3,4-c]pyrazole-2 (4H)-carboxylate (64 mg) that was produced, N,N-dimethyl ethylenediamine (51.0 mg, 0.063 mL) was added at room temperature under an argon atmosphere, after which the reaction was carried out at room temperature for 14.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (38.4 mg, 77% yield) as a white solid.

Mass spectrum (ESI, m/z):456[M+H]$^+$ $^1$H-NMR spectrum (400 MHz, DMSO-d$_6$) δ:12.34 (br s, 1H), 10.04-9.69 (m, 1H), 7.80-7.55 (m, 1H), 7.04-6.96 (m, 1H), 6.91 (d, J=7.9 Hz, 1H), 4.62 (br s, 2H), 2.38-2.25 (m, 2H), 2.22-2.06 (m, 8H), 1.64 (br s, 8H), 0.95 (s, 9H)

Embodiment 10

3-(1-(tert-butyl) cyclobutane-1-carboxamide)-N-(6-fluorobenzofuran-7-yl)-6,6-dimethyl-4,6-dihydropyrrolo [3,4-c]pyrazole-5 (1H)-carboxamide To a dehydrated toluene (1.0 mL) suspension of 6-fluorobenzofuran-7-carboxylic acid (41.7 mg) that was synthesized referencing the description in Reference Example 15 of WO2016/204153, TEA (0.040 mL) and DPPA (63.9 mg, 0.050 mL) were added sequentially at room temperature under an argon atmosphere, and reacted while stirring for 40 minutes at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (44.1 mg) that was synthesized in the same manner as in Reference Example 2, was added dropwise at 0° C., after which the reaction was carried out at 0° C. for 2 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→60:40), and the fraction containing the desired product was concentrated under reduced pressure and dried under reduced pressure to produce ethyl 3-(1-(tert-butyl) cyclobutane-1-carboxamide)-5-((6-fluorobenzofuran-7-yl) carbamoyl)-6,6-dimethyl-5,6-dihydropyrrolo [3,4-c]pyrazole-2 (4H)-carboxylate (69 mg) as a light yellow oily substance. To a THF solution (1.0 mL) of the ethyl 3-(1-(tert-butyl) cyclobutane-1-carboxamide)-5-((6-fluorobenzofuran-7-yl) carbamoyl)-6,6-dimethyl-5,6-dihydropyrrolo [3,4-c]pyrazole-2 (4H)-carboxylate (69 mg) that was produced, N,N-dimethyl ethylenediamine (0.063 mL) was added at room temperature under an argon atmosphere, after which the reaction was carried out at room temperature for 14.5 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50→30:70), and the fraction containing the target product was concentrated under reduced pressure and dried under reduced pressure. The concentrated residue produced was dissolved in an acetonitrile/water mixed solvent and lyophilized to produce the indicated compound (42.4 mg, 78% yield) as a white solid.

Mass spectrum (ESI, m/z):468[M+H]$^+$ $^1$H-NMR spectrum (400 MHz, DMSO-d$_6$) δ: 12.47-11.88 (m, 1H), 10.08-9.72 (m, 1H), 8.19 (br s, 1H), 8.01 (d, J=2.1 Hz, 1H), 7.48 (dd, J=4.9, 8.5 Hz, 1H), 7.15 (dd, J=8.5, 10.5 Hz, 1H), 6.97 (d, J=2.1 Hz, 1H), 4.67 (br s, 2H), 2.39-2.26 (m, 2H), 2.15 (br s, 2H), 1.81-1.52 (m, 8H), 0.95 (s, 9H)

Embodiment 11

3-(1-(tert-butyl) cyclobutane-1-carboxamide)-N-(2-chloro-6-fluorobenzofuran-7-yl)-6,6-dimethyl-4,6-dihydropyrrolo [3,4-c]pyrazole-5 (1H)-carboxamide To a dehydrated toluene (1.0 mL) suspension of 2-chloro-6-fluorobenzofuran-7-carboxylic acid (47.0 mg) that was synthesized referencing the description in Reference Example 39 of WO2016/204153, TEA (0.038 mL) and DPPA (60.1 mg, 0.047 mL) were added sequentially at room temperature under an argon atmosphere, and reacted while stirring for 50 minutes at room temperature followed by raising the temperature to 85° C. for 1 hour. After cooling the reaction fluid to 0° C., a dehydrated toluene solution (0.50 mL) of ethyl 3-(1-(tert-butyl) cyclobutane-1-carboxamide)-6,6-dimethyl-5,6-dihydropyrrolo [3,4-c]pyrazole-2 (4H)-carboxylate (41.3 mg) that was synthesized in the same manner as in Reference Example 2, was added dropwise at 0° C., after which the reaction was carried out at 0° C. for 4.5 hours while stirring.

After completion of the reaction, the reaction solution was diluted with ethyl acetate and washed sequentially with a saturated aqueous sodium bicarbonate solution and a saturated aqueous sodium chloride solution. The organic phase after washing was dried with anhydrous magnesium sulfate, filtered, and concentrated under reduced pressure. The concentrated residue produced was subjected to preparative column chromatography (silica gel, n-hexane:ethyl acetate=95:5→85:15→65:35), and the fraction containing the desired product was concentrated under reduced pressure and dried under reduced pressure to produce ethyl 3-(1-(tert-butyl) cyclobutane-1-carboxamide)-5-((2-chloro-6-fluorobenzofuran-7-yl) carbamoyl)-6,6-dimethyl-5,6-dihydropyrrolo [3,4-c]pyrazole-2 (4H)-carboxylate (64 mg) as a light yellow foamy substance.

To a THF solution (1.0 mL) of the ethyl 3-(1-(tert-butyl) cyclobutane-1-carboxamide)-5-((2-chloro-6-fluorobenzofuran-7-yl) carbamoyl)-6,6-dimethyl-5,6-dihydropyrrolo [3,4-c]pyrazole-2 (4H)-carboxylate (64 mg) that was produced, N,N-dimethyl ethylenediamine (0.059 mL) was added at room temperature under an argon atmosphere, after which the reaction was carried out at room temperature for 15 hours while stirring.

After completion of the reaction, a 5% aqueous potassium hydrogen sulfate solution was added to the reaction solution, stirred, and then extracted twice with ethyl acetate. The resulting total organic phase was dried using anhydrous magnesium sulfate, filtered, and concentrated under reduced pressure. The concentrated residue produced was subjected to preparative column chromatography (Diol silica gel, n-hexane:ethyl acetate=80:20→50:50), and the fraction containing the target product was concentrated under reduced pressure and dried under reduced pressure. The concentrated residue produced was dissolved in an acetonitrile/water mixed solvent and subjected to lyophilizing to produce the indicated compound (42.0 mg, 77% yield) as a white solid.

Mass spectrum (ESI, m/z):502[M+H]$^+$ $^1$H-NMR spectrum (400 MHz, DMSO-d$_6$) δ:12.51-11.79 (m, 1H), 10.00-9.70 (m, 1H), 8.36-8.14 (m, 1H), 7.44 (dd, J=4.8, 8.6 Hz, 1H), 7.20 (dd, J=8.6, 10.7 Hz, 1H), 7.05 (s, 1H), 4.67 (s, 2H), 2.38-2.27 (m, 2H), 2.21-2.09 (m, 2H), 1.72-1.60 (m, 8H), 0.95 (s, 9H)

Reference Example 1

5-(tert-butyl) 2-ethyl 3-(1-(tert-butyl) cyclobutane-1-carboxamide)-6,6-dimethylpyrrolo [3,4-c]pyrazole-2,5 (4H,6H)-dicarboxylate Oxalyl chloride (2.01 g, 1.36 mL) and DMF (11.3 mg, 0.012 mL) were added sequentially at 0° C. under an argon atmosphere to a dehydrated dichloromethane (12 mL) solution of 1-(tert-butyl) cyclobutane-1-carboxylic acid (887 mg, purchased from CHEMSPACE), followed by stirring at that temperature for 2 hours.

After completion of the reaction, the reaction solution was concentrated under reduced pressure and dried under reduced pressure.

Under an argon atmosphere, DIPEA (2.70 mL) and 5-(tert-butyl) 2-ethyl 3-amino-6,6-dimethylpyrrolo [3,4-c] pyrazole-2,5 (4H,6H)-dicarboxylate (1.05 g) [synthesized based on a method described in Journal of Medicinal Chemistry 2012, 55 (10), 4728-4739] were added sequentially at 0° C. to a solution of this concentrated residue in dehydrated dichloromethane (12 mL), followed by reacting at 0° C. for 1 hour with stirring, then at room temperature for 14.5 hours, and further in heated reflux [bath temperature: 45° C.] for 9.5 hours.

After completion of the reaction, a saturated sodium bicarbonate aqueous solution was added to the reaction solution, stirred, and then extracted twice with ethyl acetate. The resulting total organic layer was dried using anhydrous magnesium sulfate, filtered, and concentrated under reduced pressure. The concentrated residue produced was subjected to preparative column chromatography (silica gel, n-hexane: ethyl acetate=95:5→80:20→75:25), and the fraction containing the target product was concentrated under reduced pressure and dried under reduced pressure to produce the indicated compound (1.31 g, 85% yield) as a light yellow foamy substance.

Mass spectrum (ESI, m/z):463[M+H]$^+$ $^1$H-NMR spectrum (400 MHz, DMSO-d$_6$) δ:10.08-9.95 (m, 1H), 4.54-4.37 (m, 4H), 2.32-2.17 (m, 4H), 1.77-1.65 (m, 2H), 1.59 (d, J=6.1 Hz, 6H), 1.46 (d, J=9.7 Hz, 9H), 1.34 (t, J=7.1 Hz, 3H), 0.95 (s, 9H)

Reference Example 2

Ethyl 3-(1-(tert-butyl) cyclobutane-1-carboxamido)-6,6-dimethyl-5,6-dihydropyrrolo [3,4-c]pyrazole-2 (4H)-carboxylate To a dichloromethane solution (10 mL) of 5-(tert-butyl) 2-ethyl 3-(1-(tert-butyl) cyclobutane-1-carboxamide)-6,6-dimethylpyrrolo [3,4-c]pyrazole-2,5 (4H,6H)-dicarboxylate (1.39 g) that was synthesized in the same manner as in Reference Example 1, TFA (5.0 mL) was added at room temperature under an argon atmosphere, after which the reaction was carried out at room temperature for 1.5 hours while stirring.

After completion of the reaction, the reaction solution was concentrated under reduced pressure and dried under reduced pressure. Saturated sodium bicarbonate water was added to the concentrated residue, stirred for a few minutes, and then extracted three times with dichloromethane. The resulting total organic phase was washed with the saturated sodium bicarbonate aqueous solution, and then dried using anhydrous magnesium sulfate, filtered, and concentrated under reduced pressure. The concentrated residue produced was subjected to preparative column chromatography (silica gel, 1,2-dichloroethane:methanol=99:1→90:10→85:15), and the fraction containing the target product was concentrated under reduced pressure and dried under reduced pressure to produce the indicated compound (1.03 g, 93% yield) as a light brown foamy substance.

Mass spectrum (ESI, m/z):363[M+H]$^+$ $^1$H-NMR spectrum (400 MHz, DMSO-d$_6$) δ: 9.94 (s, 1H), 4.39 (q, J=7.1 Hz, 2H), 3.94 (s, 2H), 3.90 (s, 1H), 2.31-2.17 (m, 4H), 1.76-1.62 (m, 2H), 1.37-1.25 (m, 9H), 0.95-0.90 (m, 9H)

Test Example 1

CDK7 Enzyme Inhibition Test

A buffer solution was prepared by mixing HEPES buffer solution (pH 7.4), dithiothreitol (DTT), Triton X-100, and magnesium chloride (MgCl$_2$). A 500 μM [γ-$^{33}$P] ATP solution, made by diluting 10 mM ATP solution and commercial [γ-$^{33}$P] ATP solution [Perkin Elmer Code No. NEG-302H] with the buffer solution, was used. The CDK7 solution used that which was made by diluting a commercially available CDK7 [Carna biosciences, Catalog No. 04-108] with the buffer solution. The substrate solution used myelin basic protein (MBP) diluted in the buffer solution. The buffer solution, the CDK7 solution, and the substrate solution were mixed at 4° C. to prepare a reaction solution.

For the CDK7 enzyme reaction, 5 μL of the test compound solution, prepared with 10% DMSO:90% distilled water for injection, and 40 μL of the reaction solution were added to 1.5 mL microtubes at 4° C., and the microtubes were preincubated in a water bath incubator at 25° C. for 60 min. 5 μL of the 500 M [γ-$^{33}$P] ATP solution was then added, and a reaction was carried out at 30° C. for 20 minutes. While cooling to 4° C. after the reaction, a 10% trichloroacetic acid (TCA) solution was added to each microtube and mixed with a vortex mixer to stop the reaction. After standing at 4° C. for 10 minutes, centrifugal separation was performed, and the supernatant was discarded. A 2% trichloroacetic acid (TCA) solution was then added and mixed in a vortex mixer, followed by centrifugal separation, and the supernatant was discarded. This washing operation was performed twice. After washing, the precipitate was dissolved in an aqueous 1N sodium hydroxide (NaOH) solution, and the amount of energy (radioactivity) of the reaction product was measured using a liquid scintillation counter.

The inhibitory activity of the test compound against CDK7 was calculated using EXSUS (version 8.1.0, CAC EXICARE), defining as "$IC_{50}$" the concentration of the test compound that inhibits 50% of the amount of $^{33}P$ bound to MBP.

The Ki values were calculated in accordance with the following formula. In this formula, S represents the concentration of ATP in the reaction solution and Km represents the Michaelis-Menten constant.

$$Ki=IC_{50}/(1+S/Km)$$

In this study, the compounds of the present invention exhibited excellent CDK7 inhibitory activity, and the Ki values of the compounds obtained in Examples 1 through 11 were less than 50 nM.

Test Example 2

CDK2 Enzyme Inhibition Test

A buffer solution was prepared by mixing HEPES buffer solution (pH 7.4), dithiothreitol (DTT), Triton X-100, and magnesium chloride ($MgCl_2$). A 500 μM [γ-$^{33}P$] ATP solution, made by diluting 10 mM ATP solution and commercial [γ-$^{33}P$] ATP solution [Perkin Elmer Code No. NEG-302H] with the buffer solution, was used. The CDK2 solution used that which was made by diluting a commercially available CDK2 [Invitrogen, Catalog No. PV3267] with the buffer solution. The substrate solution used myelin basic protein (MBP) diluted in the buffer solution. The buffer solution, the 500 μM [γ-$^{33}P$] ATP solution, the CDK2 solution, and the substrate solution were mixed at 4° C. to prepare a reaction solution.

For the CDK2 enzyme reaction, 5 μL of the test compound solution, prepared with 10% DMSO:90% distilled water for injection, and 45 μL of the reaction solution were added to 1.5 mL microtubes at 4° C., and the microtubes were reacted in a water bath incubator at 30° C. for 20 min. While cooling to 4° C. after the reaction, a 10% trichloroacetic acid (TCA) solution was added to each microtube and mixed with a vortex mixer to stop the reaction. After standing at 4° C. for 10 minutes, centrifugal separation was performed, and the supernatant was discarded. A 2% trichloroacetic acid (TCA) solution was then added and mixed in a vortex mixer, followed by centrifugal separation, and the supernatant was discarded. This washing operation was performed twice. After washing, the precipitate was dissolved in an aqueous 1N sodium hydroxide (NaOH) solution, and the amount of energy (radioactivity) of the reaction product was measured using a liquid scintillation counter.

The inhibitory activity of the test compound against CDK2 was calculated using EXSUS (version 8.1.0, CAC EXICARE), defining as "$IC_{50}$" the concentration of the test compound that inhibits 50% of the amount of $^{33}P$ bound to MBP.

The Ki values were calculated in accordance with the following formula. In this formula, S represents the concentration of ATP in the reaction solution and Km represents the Michaelis-Menten constant.

$$Ki=IC_{50}/(1+S/Km)$$

In this study, there was low CDK2 inhibitory activity for the compounds of the present invention, and the Ki values of the compounds obtained in Examples 1 through 11 were greater than 300 nM. That is, the compounds of the present invention inhibited CDK7 with high selectivity in respect to CDK2.

Test Example 3

PLK1 Enzyme (Polo-Like Kinase) Inhibition Test

A buffer solution was prepared by mixing MOPS buffer solution (pH 7.0), dithiothreitol (DTT), and magnesium acetate ($Mg(CH_3COO)_2$). A 1 mM [γ-$^{33}P$] ATP solution, made by diluting 10 mM ATP solution and commercial [γ-$^{33}P$] ATP solution [Perkin Elmer Code No. NEG-302H] with the buffer solution, was used. The PLK1 solution used that which was made by diluting a commercially available PLK1 [Carna biosciences, Catalog No. 05-157] with the buffer solution. Casein diluted with the buffer solution was used for the substrate solution. The buffer solution, the 500 μM [γ-$^{33}P$] ATP solution, the PLK1 solution, and the substrate solution were mixed at 4° C. to prepare a reaction solution.

For the PLK1 enzyme reaction, 5 μL of the test compound solution, prepared with 10% DMSO:90% distilled water for injection, and 45 μL of the reaction solution were added to 1.5 mL microtubes at 4° C., and the microtubes were reacted in a water bath incubator at 30° C. for 20 min. While cooling to 4° C. after the reaction, a 10% trichloroacetic acid (TCA) solution was added to each microtube and mixed with a vortex mixer to stop the reaction. After standing at 4° C. for 10 minutes, centrifugal separation was performed, and the supernatant was discarded. A 2% trichloroacetic acid (TCA) solution was then added and mixed in a vortex mixer, followed by centrifugal separation, and the supernatant was discarded. This washing operation was performed twice. After washing, the precipitate was dissolved in an aqueous 1N sodium hydroxide (NaOH) solution, and the amount of energy (radioactivity) of the reaction product was measured using a liquid scintillation counter.

The inhibitory activity of the test compound against PLK1 was calculated using EXSUS (version 8.1.0, CAC EXICARE), defining as "$IC_{50}$" the concentration of the test compound that inhibits 50% of the amount of $^{33}P$ bound to casein.

The Ki values were calculated in accordance with the following formula. In this formula, S represents the concentration of ATP in the reaction solution and Km represents the Michaelis-Menten constant.

$$Ki=IC_{50}/(1+S/Km)$$

In this study, there was low PLK1 inhibitory activity for the compounds of the present invention, and the Ki values of the compounds obtained in Examples 1 through 11 were greater than 5000 nM. That is, the compounds of the present invention inhibited CDK7 with high selectivity in respect to PLK1.

Test Example 4

Human Colorectal Cancer (HCT-116) Cell Growth Inhibition Study

The method of Simak et al. (Cancer Research, 69, 6208 (2009)) was modified to measure the inhibition effect on human colon cancer cell growth.

A human colorectal cancer cell line (HCT-116, obtained from DS Pharma Biomedical Co., Ltd.) was cultured in McCoy's 5A medium (Thermo Fisher Scientific) containing 10% fetal bovine serum (FBS) (Thermo Fisher Scientific), 1% penicillin/streptomycin/amphotericin B (Thermo Fisher Scientific), and seeded in a 96-well plate at 0.5 through $2.0\times10^3$ cells/well. After incubation overnight in a carbon dioxide gas incubator, the medium was replaced with new medium the following day, and the test compound (dissolved in DMSO (DMSO final concentration: 0.1%)) was added, and the medium was placed in a carbon dioxide gas incubator. After 3 days of incubation, light absorption was measured using In Vitro Toxicology Assay Kit Sulforhodamine B based (Sigma) or CellTiter-Glo (Promega).

The cell proliferation inhibition rate for each concentration was calculated from the test compound concentration and the measured light absorption, and the concentration of the test compound required to inhibit cell proliferation by 50% ($IC_{50}$ value) was calculated using EXSUS (version 8.1.0, CAC Croit).

In this study, the compounds of the present invention exhibited excellent HCT-116 cell growth inhibitory activity, and the $IC_{50}$ values of the compounds obtained in Examples 1 through 11 were less than 50 nM.

Test Example 5

Mouse Melanoma (B16F10) Cell Growth Inhibition Test

Mouse melanoma cells (B16F10) (Cat. No. TKG0348, Center for Medicinal Cell Resources, Institute of Development, Aging and Cancer, Tohoku University) were cultured in DMEM medium (GIBCO REF. 11965-092) containing 10% fetal bovine serum (FBS) (GIBCO REF. 10082-147), 1% penicillin/streptomycin/amphotericin B (GIBCO REF. 15240-096), and 1 mM sodium pyruvate (GIBCO REF. 11360-070), and seeded in a 96-well plate at 0.5 through $2.0\times10^3$ cells/well. After the cells were incubated overnight in a carbon dioxide gas incubator, and further incubated for 3 days in a medium containing a DMSO solution (DMSO final concentration: 0.1%) of the test compound, the ATP level was measured using CellTiter-Glo (Promega).

The cell proliferation inhibition rate for each concentration was calculated from the test compound concentration and the amount of ATP, and the concentration of the test compound required to inhibit cell proliferation by 50% ($GI_{50}$ value) was calculated using EXSUS (version 8.1.0, CAC Croit).

Test Example 6

Human Breast Cancer (MCF-7) Cell Growth Inhibition Test

The method of Simak et al. (Cancer Research, 69, 6208 (2009)) was modified to measure the inhibition effect on human breast cancer cell growth.

A human breast cancer cell line (MCF-7, obtained from DS Pharma Biomedical Co., Ltd.) was cultured in an MEM medium containing 10% FBS and non-essential amino acids, and seeded in a 96-well plate at $3\times10^3$ cells/well. After incubation overnight in a carbon dioxide gas incubator, the medium that included 10% FBS and the non-essential amino acids was replaced with new medium the following day, and the test compound (dissolved in DMSO (DMSO final concentration: 0.1%)) was added, and the medium was placed in a carbon dioxide gas incubator. After 3 days of incubation, light absorption was measured using In Vitro Toxicology Assay Kit Sulforhodamine B based (Sigma).

The cell proliferation inhibition rate for each concentration was calculated from the test compound concentration and the measured light absorption of Sulforhodamine B, and the concentration of the test compound required to inhibit cell proliferation by 50% ($IC_{50}$ value) was calculated using EXSUS (version 8.1.0, CAC EXICARE).

Test Example 7

In Vivo Tumor Growth Inhibition Study in Mice with Subcutaneous Transplantation of Mouse Melanoma Cells (B16F10)

Mouse melanoma cells (B16F10) (Cat. No. TKG0348, Center for Medicinal Cell Resources, Institute of Development, Aging and Cancer, Tohoku University) were cultured in DMEM medium (GIBCO REF. 11965-092) containing 10% fetal bovine serum (FBS) (GIBCO REF. 10082-147), 1% penicillin/streptomycin/amphotericin B (GIBCO REF. 15240-096), 1 mM sodium pyruvate (GIBCO REF. 11360-070), and adjusted to $1.0\times10^7$ cells/mL using a PBS (GIBCO REF. 10010-031). The prepared cell suspension was injected under the skin on the right side of the abdomen of C57BL/6 mice (female, supplied by SLC Japan) at 0.1 mL per mouse. After a prescribed amount of time had elapsed, the long and short dimensions (mm) of the tumors were with an electronic caliper (Mitutoyo Cat. 500-712-10), and the volumes of the tumors were calculated using the following formula:

$$\text{Tumor volume (mm}^3) = (\text{long dimension}) \times (\text{short dimension}) \times (\text{short dimension}) \times 0.5$$

Those subjects with tumor volumes the range of 50-200 $mm^3$ were selected and divided into groups with similar tumor volumes, and 250 g/mouse anti-PD-1 antibodies (BioXcell) or 250 g/mouse IgG2a (BioXcell) were administered intraperitoneally, followed by oral administration of the test compound (25 mg/kg or 100 mg/kg) or of the solvent only, to the respective groups. With the date of the initial dosing as day 0, the anti-PD-1 antibody or Rat IgG2a was administered intraperitoneally on days 0 and 3, and the test compound or solvent alone was administered orally once a day from day 0 to day 6. On day 7, the long and short dimensions of the tumors were measured, and the tumor volumes were calculated. The tumor volume growth inhibition rate for each group was calculated with the tumor volume growth rate from day 0 for the Rat IgG2a and solvent groups defined 100.

Test Example 8

Tumor Growth Inhibition Study in Mice with Subcutaneous Transplantation of Human Colon Cancer Cells (HCT116)

A human colon carcinoma cell line (HCT-116) was cultured in McCoy's 5A medium containing 10% FBS and 1% penicillin/streptomycin/amphotericin B, and adjusted to $1.0\times10^8$ cells/mL using PBS or Hanks' solution (HBSS (−)). The prepared cell suspension was injected under the skin on the right side of the abdomen of male BALB-line nude mice (supplied by Charles River Japan) at 0.1 mL per mouse. After a prescribed amount of time had elapsed, the long and short dimensions (mm) of the tumors were with an electronic caliper, and the volumes of the tumors were calculated using the following formula:

Tumor volume (mm³)=(long dimension)×(short dimension)×(short dimension)×0.5

Individual subjects with tumor volumes in the range of 50-200 mm³ were selected and divided into groups with similar tumor volumes, and then the test compound or the solvent alone was administered orally repeatedly, and the body weights and tumor dimensions were measured. The test compound was suspended in a 0.5 w/v % methylcellulose solution (0.5% MC) (Wako Pure Chemical Co., Ltd.) and administered orally at 10 mL/kg repeatedly. The tumor volume of the control group was defined as 100%, and the tumor volume inhibition rate (%) was calculated for each dosage of the test compound.

From the results of test examples 1 through 4, the compounds of the present invention have excellent CDK7 inhibitory activity and high selectivity, and are useful, for example, as therapeutic and/or prophylactic agents for cancer.

The invention claimed is:

1. A compound or a pharmacologically acceptable salt thereof, wherein the compound is of formula (I):

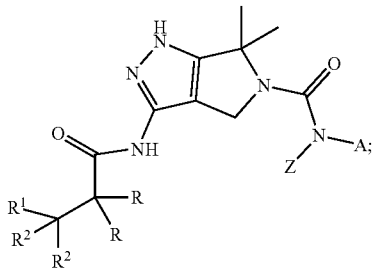

(I)

wherein:

each R together with the carbon atom to which they are attached form a cyclobutyl group or a cyclopropyl group;

$R^1$, $R^2$, and $R^3$ are each independently a substituted or unsubstituted linear or branched $C_{1-4}$ alkyl group;

A is a substituted or unsubstituted $C_{6-10}$ aryl group or a substituted or unsubstituted heteroaryl group;

Z is a hydrogen atom or a substituted or unsubstituted $C_{1-6}$ alkyl group; or A and Z are bonded together with the nitrogen atom to which they are attached to form a substituted or unsubstituted bicyclic fused heteroaryl group.

2. The compound of claim 1, wherein the compound of formula (I) is a compound of formula (III) or a pharmacologically acceptable salt thereof:

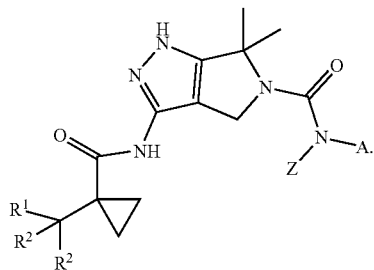

(III)

3. The compound of claim 1, wherein the compound of formula (I) is of compound of formula (IV) or a pharmacologically acceptable salt thereof:

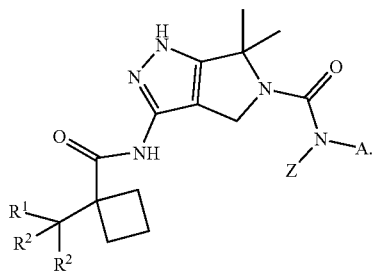

(IV)

4. The compound of claim 1, wherein $R^1$, $R^2$, and $R^3$ are each independently a methyl group or an ethyl group.

5. The compound of claim 1, wherein Z is a hydrogen atom.

6. The compound of claim 1, wherein A is a phenyl group, optionally substituted with 1 to 3 groups independently selected from a halogen atom and a $C_{1-3}$ alkyl group.

7. The compound of claim 1, wherein A is a benzofuranyl group, optionally substituted with 1 to 3 groups independently selected from a halogen atom and a $C_{1-3}$ alkyl group.

8. The compound of claim 1 or a pharmacologically acceptable salt thereof selected from the group consisting of:
3-(1-(tert-butyl) cyclobutane-1-carboxamide)-N-(2-fluorophenyl)-6,6-dimethyl-4,6-dihydropyrrolo [3,4-c] pyrazole-5 (1H)-carboxamide,
3-(1-(tert-butyl) cyclobutane-1-carboxamide)-N-(o-tolyl)-6,6-dimethyl-4,6-dihydropyrrolo [3,4-c]pyrazole-5 (1H)-carboxamide,
3-(1-(tert-butyl) cyclobutane-1-carboxamide)-N-(2-chloro-6-methylphenyl)-6,6-dimethyl-4,6-dihydropyrrolo [3,4-c]pyrazole-5 (1H)-carboxamide,
3-(1-(tert-butyl) cyclobutane-1-carboxamide)-N-(5-fluoro-2-methylphenyl)-6,6-dimethyl-4,6-dihydropyrrolo [3,4-c]pyrazole-5 (1H)-carboxamide,
3-(1-(tert-butyl) cyclobutane-1-carboxamide)-N-(2,5-dimethylphenyl)-6,6-dimethyl-4,6-dihydropyrrolo [3,4-c]pyrazole-5 (1H)-carboxamide,
3-(1-(tert-butyl) cyclobutane-1-carboxamide)-N-(2,6-dimethylchlorophenyl)-6,6-dimethyl-4,6-dihydropyrrolo [3,4-c]pyrazole-5 (1H)-carboxamide,
3-(1-(tert-butyl) cyclobutane-1-carboxamide)-N-(2-chloro-6-fluorophenyl)-6,6-dimethyl-4,6-dihydropyrrolo [3,4-c]pyrazole-5 (1H)-carboxamide,
N-(2-bromo-6-methylphenyl)-3-(1-(tert-butyl) cyclobutane-1-carboxamide)-6,6-dimethyl-4,6-dihydropyrrolo [3,4-c]pyrazole-5 (1H)-carboxamide, 3-(1-(tert-butyl) cyclobutane-1-carboxamide)-N-(2-fluoro-3,6-dimethylphenyl)-6,6-dimethyl-4,6-dihydropyrrolo [3,4-c]pyrazole-5 (1H)-carboxamide, 3-(1-(tert-butyl) cyclobutane-1-carboxamide)-N-(6-fluorobenzofuran-7-yl)-6,6-dimethyl-4,6-dihydropyrrolo [3,4-c]pyrazole-5 (1H)-carboxamide, and 3-(1-(tert-butyl) cyclobutane-1-carboxamide)-N-(2-chloro-6-fluorobenzofuran-7-yl)-6,6-dimethyl-4,6-dihydropyrrolo [3,4-c]pyrazole-5 (1H)-carboxamide.

9. A pharmaceutical composition comprising the compound of claim 1 or pharmacologically acceptable salt thereof and a pharmaceutically acceptable carrier.

10. A method of treating cancer in a subject in need thereof, the method comprising administering to the subject the compound of claim 1 or a pharmacologically acceptable salt thereof.

11. The method of claim 10, wherein the cancer is multiple myeloma, chronic myelogenous leukemia, a hematological tumor, a hematologic malignancy, childhood leukemia, a childhood lymphoma, Hodgkin's disease, a lymphocytic lymphoma, a cutaneous lymphoma, acute leukemia, chronic leukemia, acute lymphoblastic leukemia, acute myelocytic leukemia, chronic myelocytic leukemia, a plasma cell neoplasm, a lymphocyte-like neoplasm, or an AIDS-related cancer.

12. The method of claim 10, wherein the cancer is colorectal cancer, bladder cancer, breast cancer, colon cancer, kidney cancer, liver cancer, lung cancer, small cell lung cancer, non-small cell lung cancer, head and neck cancer, esophageal cancer, gallbladder cancer, ovarian cancer, pancreatic cancer, stomach cancer, cervical cancer, thyroid cancer, prostate cancer, skin cancer, a fibrosarcoma, a rhabdomyosarcoma, an astrocytoma, a neuroblastoma, a glioma or schwannoma, a melanoma, a seminoma, a teratoid carcinoma, an osteosarcoma, a xeroderma pigmentosum, a keratinocytoma, a follicular carcinoma of the thyroid, or a Kaposi's sarcoma.

13. The method of claim 10, wherein the cancer is associated with abnormal activation of CDK7.

14. The method of claim 10, wherein the cancer is colorectal cancer, melanoma, breast cancer, or colon cancer.

15. A method of treating rheumatoid arthritis in a subject in need thereof, the method comprising administering to the subject the compound of claim 1 or a pharmacologically acceptable salt thereof, thereby treating rheumatoid arthritis.

16. The compound of claim 2, wherein $R^1$, $R^2$, and $R^3$ are each independently a methyl group or an ethyl group; Z is a hydrogen atom; and A is a phenyl group, optionally substituted with 1 to 3 groups independently selected from the group consisting of a halogen atom and a $C_{1-3}$ alkyl group.

17. The compound of claim 3, wherein $R^1$, $R^2$, and $R^3$ are each independently a methyl group or an ethyl group; Z is a hydrogen atom; and A is a phenyl group, optionally substituted with 1 to 3 groups independently selected from the group consisting of a halogen atom and a $C_{1-3}$ alkyl group.

* * * * *